US008748466B2

(12) United States Patent
Abramite et al.

(10) Patent No.: US 8,748,466 B2
(45) Date of Patent: Jun. 10, 2014

(54) ISOXAZOLE DERIVATIVES USEFUL AS ANTIBACTERIAL AGENTS

(75) Inventors: Joseph Alan Abramite, Mystic, CT (US); Matthew Frank Brown, Stonington, CT (US); Jinshan Michael Chen, Madison, CT (US); Michael Joseph Melnick, Portage, MI (US); Justin Ian Montgomery, Ledyard, CT (US); Usa Reilly, West Haven, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/110,157

(22) PCT Filed: Mar. 23, 2012

(86) PCT No.: PCT/IB2012/051406
§ 371 (c)(1),
(2), (4) Date: Oct. 7, 2013

(87) PCT Pub. No.: WO2012/137094
PCT Pub. Date: Oct. 11, 2012

(65) Prior Publication Data
US 2014/0024690 A1  Jan. 23, 2014

Related U.S. Application Data

(60) Provisional application No. 61/473,540, filed on Apr. 8, 2011.

(51) Int. Cl.
*C07D 261/08* (2006.01)
*C07D 413/04* (2006.01)

(52) U.S. Cl.
USPC .......................................... 514/378; 548/247

(58) Field of Classification Search
CPC .............................. C07D 261/08; C07D 413/04
USPC ............................................ 514/378; 548/247
See application file for complete search history.

(56) References Cited

U.S. PATENT DOCUMENTS

| 4,769,461 | A | 9/1988 | Musser et al. |
| 5,110,831 | A | 5/1992 | Magolda et al. |
| 6,673,965 | B1 | 1/2004 | Ward et al. |
| 2005/0014806 | A1* | 1/2005 | Farrerons Gallemi et al. ............... 514/378 |
| 2005/0119305 | A1 | 6/2005 | Naka et al. |
| 2006/0247271 | A1 | 11/2006 | Bruton |
| 2006/0276409 | A1 | 12/2006 | Hunter et al. |
| 2008/0085893 | A1 | 4/2008 | Yang et al. |
| 2008/0234297 | A1 | 9/2008 | Qian et al. |
| 2011/0178042 | A1 | 7/2011 | Brown et al. |
| 2012/0232083 | A1 | 9/2012 | Reilly et al. |
| 2012/0258948 | A1 | 10/2012 | Brown et al. |

FOREIGN PATENT DOCUMENTS

| EP | 1437349 | 7/2004 |
| WO | 0130747 | 5/2001 |
| WO | 2004062601 | 7/2004 |
| WO | 2004067502 | 8/2004 |
| WO | 2006063281 | 6/2006 |
| WO | 2006118155 | 11/2006 |
| WO | 2006124897 | 11/2006 |
| WO | 2007069020 | 6/2007 |
| WO | 2008045671 | 4/2008 |
| WO | 2008105515 | 9/2008 |
| WO | 2008115262 | 9/2008 |
| WO | 2009008905 | 1/2009 |
| WO | 2010017060 | 2/2010 |
| WO | 2010024356 | 3/2010 |
| WO | 2010031750 | 3/2010 |
| WO | 2010032147 | 3/2010 |
| WO | 2010100475 | 9/2010 |
| WO | 2011073845 | 6/2011 |
| WO | 2012120397 | 9/2012 |
| WO | 2012137094 | 10/2012 |
| WO | 2012137099 | 10/2012 |

OTHER PUBLICATIONS

"455710(Antibiotics and Antibacterial Drugs)", Annual Drug Data Report, Jan. 1, 2007, p. 629, 29(7).
Barlaam, B., et al., "New Alpha-Substituted Succinate-Based Hydroxamic Acids As TNFALPHA Convertase Inhibitors", Journal of Medicinal Chemistry, Jan. 1, 1999, pp. 4890-4908, 42(23).
Clements, J.M., et al., "Antimicrobial Activities and Characterization of Novel Inhibitors of LpxC", Antimicrobial Agents and Chemotherapy, American Society for Microbiology, Jun. 1, 2002, pp. 1793-1799, 46(6).
Conreaux, D., et I., "A practical procedure for the selective N-alkylation of 4-alkoxy-2-pyridones and its use in a sulfone-mediated synthesis of N-methyl-4-methoxy-2-pyridone", Tetrahedron Letters, 2005, pp. 7917-7920, 46(46).
Dube, Peter H., et al., "Protective Role of Interleukin-6 During *Yersinia enterocolitica* Infection Is Mediated through the Modulation of Inflammatory Cytokines", Infection and Immunity, Jun. 2004, pp. 3561-3570, 72(6).
English Translation of International Patent Application WO 2008/105515 publication date Sep. 4, 2008.
Gennadios, H.A., et al., "Mechanistic Inferences from the Binding of Ligands to LpxC, a Metal-Dependent Deacetylase", Biochemistry, 2006, pp. 7940-7948, 45(26).
Gipstein, E., et al., "Synthesis and Polymerization of Alkyl.α.-(Alkylsulfonyl)acrylates1a", Journal of Organic Chemistry, 1980, pp. 1486-1489, 45(8).
Hennigan, Stephanie, et al., "Interleukin-6 Inhibitors in the Treatment of Rheumatoid Arthritis", Therapeutics and Clinical Risk Management, 2008, pp. 767-775, 4(4).
Imanishi, Jiro, "Expression of Cytokines in Bacterial and Viral Infections and Their Biochemical Aspects", The Japanese Biochemical Society, 2000, pp. 525-530, 127(4).
International Patent Application No. PCT/IB2010/055596, publication No. WO 2011/073845,Search Report and Written Opinion mailed Mar. 23, 2011, 15 pages.

(Continued)

*Primary Examiner* — Kamal Saeed
(74) *Attorney, Agent, or Firm* — John A. Wichtowski

(57) ABSTRACT

The present invention is directed to a new class of hydroxamic acid derivatives, their use as LpxC inhibitors and, more specifically, their use to treat bacterial infections.

13 Claims, No Drawings

(56) References Cited

OTHER PUBLICATIONS

Iupac, E.D., et al., "alkyl groups", Compendium of Chemical Terminology: IUPAC Recommendations; http://www.iupac.org/goldbook/A00228.pdf Jan. 1, 1997.
Kirsch, P., et al., "Super-Fluorinated Liquid Crystals: Towards the Limits of Polarity", European Journal Organic Chemistry, Jul. 2008, pp. 3479-3487, 2008(20).
Kwok, A., et al., "Helicobacter Pylori Eradication Therapy: Indications, efficacy and Safety", Expert Opinion Drug Safety, May 2008, pp. 271-281, 7(3).
International Patent Application No. PCT/IB2009/053809, PCT International Search Report (ISR), mailed Apr. 4, 2010, 7 pages.
International Patent Application No. PCT/IB2009/053809, PCT International Written Opinion, mailed Apr. 4, 2010, 7 pages.
International Patent Application No. PCT/IB2012/050812 PCT International Search Report (ISR) and Written Opinion mailed Apr. 23, 2012.
Product Label—ACTEMRA (toclizumab) Injection, for intravenous infusion; revised Apr. 2013, pp. 1-35.
Qu, W., et al., "Quick Assembly of 1,4-Diphenyltriazoles as Probes Targeting β-Amyloid Aggregates in Alzheimer's Disease", Journal of Medicinal Chemistry, 2007, pp. 3380-3387, 50(14).
Raetz, Christian, H., et al., "Lipid A Modification Systems in Gram-Negative Bacteria", Annual Review Biochemistry, 2007, pp. 295-329, vol. 76.
Rice, Louis B., "Unmet Medical Needs in Antibacterial Therapy", Biochemical Pharmacology, Mar. 30, 2006, pp. 991-995, 71(7).
Wang, Y., et al., "A novel and efficient synthesis of terminal arylacetylenes via Sonogashira coupling reactions catalysed by MCM-41-supported bidentate phosphine palladium (0) complex", Journal of Chemical Research, Dec. 2007, pp. 728-732, 2007(12).
Apfel, Christian et al., "Hydroxamic Acid Derivatives as Potent Peptide Deformylase Inhibitors and Antibacterial Agents", Journal of Medicinal Medicinal Chemistry, Jun. 15, 2000, pp. 2324-2331, 43(12).
Brown, Matthew F., et al., "Potent Inhibitors of LpxC for the Treatment of Gram-Negative Infections", Journal of Medicinal Chemistry, Dec. 18, 2011, pp. 914-923, 55(18).
International Patent Application No. PCT/IB2012/051406 PCT International Search Report (ISR) and Written Opinion mailed Oct. 7, 2012, 5 pages.

* cited by examiner

ISOXAZOLE DERIVATIVES USEFUL AS ANTIBACTERIAL AGENTS

This application is a national stage application under 35 U.S.C. 371 of PCT/IB2012/051406, filed on Mar. 23, 2012, which claims the benefit of U.S. Provisional Patent Application No. 61/473,540, filed on Apr. 8, 2011, the disclosures of which are hereby incorporated by reference in their entirety.

FIELD OF THE INVENTION

This invention relates to novel hydroxamic acid derivatives. The invention also relates to methods of using such compounds in the treatment of bacterial infections (especially Gram-negative infections) and to pharmaceutical compositions containing such compounds.

BACKGROUND OF THE INVENTION

Infection by Gram-negative bacteria such as *Pseudomonas aeruginosa*, Extended Spectrum β-lactamase producing (ESBL) Enterobacteriaceae, and *Acinetobacter baumannii* is a major health problem, especially in the case of hospital-acquired infections. In addition, there is an increasing level of resistance to current antibiotic therapies, which severely limits treatment options. For example, in 2002, 33% of *Pseudomonas aeruginosa* infections from intensive care units were resistant to fluoroquinolones, while resistance to imipenem was 22% (CID 42: 657-68, 2006). In addition, multi-drug resistant (MDR) infections are also increasing; in the case of *Pseudomonas aeruginosa*, MDR increased from 4% in 1992 to 14% in 2002 (Biochem Pharm 71: 991, 2006).

Gram-negative bacteria are unique in that their outer membrane contains lipopolysaccharide (LPS), which is crucial for maintaining membrane integrity, and is essential for bacterial viability (reviewed in Ann. Rev. Biochem 76: 295-329, 2007). The major lipid component of LPS is Lipid A, and inhibition of Lipid A biosynthesis is lethal to bacteria. Lipid A is synthesized on the cytoplasmic surface of the bacterial inner membrane via a pathway that consists of nine different enzymes. These enzymes are highly conserved in most Gram-negative bacteria. LpxC [UDP-3-O—(R-3-hydroxymyristoyl)-N-acetylglucosamine deacetylase] is the enzyme that catalyzes the first committed step in the Lipid A biosynthetic pathway, the removal of the N-acetyl group of UDP-3-O—(R-3-hydroxymyristoyl)-N-acetylglucosamine. LpxC is a $Zn^{2+}$ dependent enzyme that has no mammalian homologue, making it a good target for the development of novel antibiotics. Several inhibitors of LpxC with low nM affinity have been reported (Biochemistry 45: 7940-48, 2006).

SUMMARY OF THE INVENTION

A new class of LpxC inhibitors has been discovered. These compounds, or their pharmaceutically acceptable salts, can be represented by Formula I and Formula II below:

Formula I

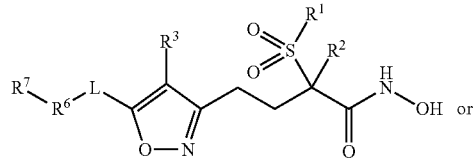

or

Formula II

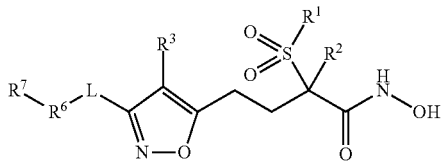

wherein
$R^1$ is $(C_1$-$C_3)$alkyl;
$R^2$ is hydrogen or $(C_1$-$C_3)$alkyl;
$R^3$ is hydrogen, $(C_1$-$C_3)$alkoxy, $(C_1$-$C_3)$alkyl, cyano, $(C_1$-$C_3)$haloalkoxy, $(C_1$-$C_3)$haloalkyl, halogen, or hydoxy;
L is a bond, —$(CH_2)_n$—, —$(CH_2)_nO(CH_2)_p$—, —$(CH_2)_nS(CH_2)_p$—, —$(CH_2)_nNR^4(CH_2)_p$—, —$(CH_2)_nSO_2NR^4(CH_2)_p$—, —$(CH_2)_nNR^4SO_2(CH_2)_p$—, —$(CH_2)_nCONR^4(CH_2)_p$—, or —$(CH_2)_nNR^4CO(CH_2)_p$—;
$R^4$ and $R^5$ are independently hydrogen, $(C_1$-$C_6)$alkyl, $(C_1$-$C_6)$alkylcarbonyl, $(C_3$-$C_8)$cycloalkyl, $(C_3$-$C_8)$cycloalkyl$(C_1$-$C_6)$alkyl, or formyl;
n is 0, 1, 2, 3, or 4;
p is 0, 1, 2, 3, or 4;
$R^6$ is $(C_1$-$C_6)$alkoxy$(C_1$-$C_6)$alkyl, $(C_1$-$C_6)$alkoxycarbonyl, $(C_1$-$C_6)$alkylcarbonyl, $(C_1$-$C_6)$alkyl-$NR^4$—$(C_1$-$C_6)$alkyl, $(C_1$-$C_6)$alkylthio$(C_1$-$C_6)$alkyl, $(C_1$-$C_6)$alkylthiocarbonyl, $(C_6$-$C_{12})$aryl, $(C_6$-$C_{12})$aryloxy, $(C_6$-$C_{12})$arylthio, $(C_6$-$C_{12})$aryl-$NR^4$—, $(C_3$-$C_8)$cycloalkyl, $(C_3$-$C_8)$cycloalkyloxy, $(C_3$-$C_8)$cycloalkylthio, $(C_3$-$C_8)$cycloalkyl-$NR^4$—, $(C_5$-$C_{12})$heteroaryl, $(C_5$-$C_{12})$heteroaryloxy, $(C_5$-$C_{12})$heteroarylthio, $(C_5$-$C_{12})$heteroaryl-$NR^4$—, $(C_3$-$C_{13})$heterocycle, $(C_3$-$C_{13})$heterocycleoxy, $(C_3$-$C_{13})$heterocyclethio, $(C_3$-$C_{13})$heterocycle-$NR^4$—, hydroxy$(C_1$-$C_{10})$alkyl, mercapto$(C_1$-$C_6)$alkyl, $(NR^4R^5)$alkyl, or $(NR^4R^5)$carbonyl; and
$R^7$ is absent, $(C_6$-$C_{12})$aryl, $(C_6$-$C_{12})$aryl$(C_1$-$C_6)$alkyl, $(C_3$-$C_8)$cycloalkyl, $(C_3$-$C_8)$cycloalkyl$(C_1$-$C_6)$alkyl, $(C_5$-$C_{12})$heteroaryl, $(C_5$-$C_{12})$heteroaryl$(C_1$-$C_6)$alkyl, $(C_3$-$C_{13})$heterocycle, or $(C_3$-$C_{13})$heterocycle$(C_1$-$C_6)$alkyl.

The compounds of Formula I and Formula II exhibit antibacterial activity, especially against Gram-negative organisms. They may be used to treat bacterial infections in mammals, especially humans. The compounds may also be used for veterinary applications, such as treating infections in livestock and companion animals.

The compounds of Formula I and Formula II are useful for treating a variety of infections; especially Gram-negative infections including nosocomial pneumonia, urinary tract infections, systemic infections (bacteremia and sepsis), skin and soft tissue infections, surgical infections, intraabdominal infections, lung infections (including those in patients with cystic fibrosis), *Helicobacter pylori* (and relief of associated gastric complications such as peptic ulcer disease, gastric carcinogenesis, etc.), endocarditis, diabetic foot infections, osteomyelitis, and central nervous system infections.

In order to simplify administration, the compounds will typically be admixed with at least one excipient and formulated into a pharmaceutical dosage form. Examples of such dosage forms include tablets, capsules, solutions/suspensions for injection, aerosols for inhalation, cream/ointments for topical, otic or ophthalmic use, and solutions/suspensions for oral ingestion.

DETAILED DESCRIPTION OF THE INVENTION

The headings within this document are only being utilized to expedite its review by the reader. They should not be construed as limiting the invention or claims in any manner.

In one embodiment, the present invention provides compounds of Formula I and Formula II wherein $R^1$ is $(C_1\text{-}C_3)$ alkyl; $R^2$ is $(C_1\text{-}C_3)$alkyl; $R^3$ is hydrogen; L is a bond, —$(CH_2)_n$—, —$(CH_2)_nO(CH_2)_p$—, —$(CH_2)_nS(CH_2)_p$—, —$(CH_2)_nNR^4(CH_2)_p$—, —$(CH_2)_nSO_2NR^4(CH_2)_p$—, —$(CH_2)_nCONR^4(CH_2)_p$—, or —$(CH_2)_nNR^4CO(CH_2)_p$—; $R^4$ and $R^5$ are independently hydrogen, $(C_1\text{-}C_6)$alkyl, or $(C_3\text{-}C_8)$cycloalkyl; n is 0, 1, or 2; p is 0, 1, or 2; $R^6$ is $(C_1\text{-}C_6)$ alkoxy$(C_1\text{-}C_6)$alkyl, $(C_1\text{-}C_6)$alkoxycarbonyl, $(C_1\text{-}C_6)$alkylthiocarbonyl, $(C_6\text{-}C_{12})$aryl, $(C_6\text{-}C_{12})$aryloxy, $(C_3\text{-}C_8)$ cycloalkyl, $(C_5\text{-}C_{12})$heteroaryl, hydroxy$(C_1\text{-}C_{10})$alkyl, or $(NR^4R^5)$carbonyl; and $R^7$ is absent or $(C_3\text{-}C_{13})$heterocycle.

In another embodiment, the present invention provides compounds of Formula I and Formula II wherein $R^1$ is methyl; $R^2$ is methyl; $R^3$ is hydrogen; L is a bond, —$(CH_2)_n$—, —$(CH_2)_nO(CH_2)_p$—, —$(CH_2)_nS(CH_2)_p$—, —$(CH_2)_nNR^4(CH_2)_p$—, —$(CH_2)_nSO_2NR^4(CH_2)_p$—, —$(CH_2)_nCONR^4(CH_2)_p$—, or —$(CH_2)_nNR^4CO(CH_2)_p$—; $R^4$ is hydrogen, $(C_1\text{-}C_6)$alkyl, or $(C_3\text{-}C_8)$cycloalkyl; n is 0, 1, or 2; p is 0, 1, or 2; $R^6$ is $(C_6\text{-}C_{12})$aryl or $(C_6\text{-}C_{12})$aryloxy, wherein the $(C_6\text{-}C_{12})$aryl group for each is phenyl optionally substituted with 1, 2, or 3 substituents that are independently $(C_1\text{-}C_6)$alkoxy, $(C_1\text{-}C_6)$alkyl, halo$(C_1\text{-}C_6)$alkoxy, halogen, or methylenedioxy; and $R^7$ is absent or $(C_3\text{-}C_{13})$heterocycle, wherein the $(C_3\text{-}C_{13})$heterocycle is morpholinyl.

In another embodiment, the present invention provides compounds of Formula I and Formula II wherein $R^1$ is methyl; $R^2$ is methyl; $R^3$ is hydrogen; L is a bond, —$(CH_2)_2$—, —$O(CH_2)$—, —$(CH_2)O(CH_2)$—, —$S(CH_2)$—, —$(CH_2)_2NR^4(CH_2)$—, —$SO_2NR^4(CH_2)$—, or —$CONR^4(CH_2)$—; $R^4$ is hydrogen, $(C_1\text{-}C_6)$alkyl, or $(C_3\text{-}C_8)$ cycloalkyl; $R^6$ is $(C_6\text{-}C_{12})$aryl or $(C_6\text{-}C_{12})$aryloxy, wherein the $(C_6\text{-}C_{12})$aryl group for each is phenyl optionally substituted with 1, 2, or 3 substituents that are independently $(C_1\text{-}C_6)$alkoxy, $(C_1\text{-}C_6)$alkyl, halo$(C_1\text{-}C_6)$alkoxy, halogen, or methylenedioxy; and $R^7$ is absent or $(C_3\text{-}C_{13})$heterocycle, wherein the $(C_3\text{-}C_{13})$heterocycle is morpholinyl.

In another embodiment, the present invention provides compounds of Formula I and Formula II wherein $R^1$ is methyl; $R^2$ is methyl; $R^3$ is hydrogen; L is a bond, —$(CH_2)_2$—, —$O(CH_2)$—, —$(CH_2)O(CH_2)$—, —$S(CH_2)$—, —$(CH_2)_2NR^4(CH_2)$—, —$SO_2NR^4(CH_2)$—, or —$CONR^4(CH_2)$—; $R^4$ is hydrogen, $(C_1\text{-}C_6)$alkyl, or $(C_3\text{-}C_8)$ cycloalkyl; $R^6$ is $(C_6\text{-}C_{12})$aryl or $(C_6\text{-}C_{12})$aryloxy, wherein the $(C_6\text{-}C_{12})$aryl group for each is phenyl optionally substituted with 1, 2, or 3 substituents that are independently $(C_1\text{-}C_6)$alkoxy, $(C_1\text{-}C_6)$alkyl, halo$(C_1\text{-}C_6)$alkoxy, halogen, or methylenedioxy; and $R^7$ is absent.

In another embodiment, the present invention provides compounds of Formula I and Formula II wherein $R^1$ is methyl; $R^2$ is methyl; $R^3$ is hydrogen; L is a bond, —$(CH_2)_n$—, —$(CH_2)_nO(CH_2)_p$—, —$(CH_2)_nS(CH_2)_p$—, —$(CH_2)_nNR^4(CH_2)_p$—, —$(CH_2)_nSO_2NR^4(CH_2)_p$—, —$(CH_2)_nCONR^4(CH_2)_p$—, or —$(CH_2)_nNR^4CO(CH_2)_p$—; $R^4$ is hydrogen, $(C_1\text{-}C_6)$alkyl, or $(C_3\text{-}C_8)$cycloalkyl; n is 0, 1, or 2; p is 0, 1, or 2; $R^6$ is $(C_5\text{-}C_{12})$heteroaryl, wherein the $(C_5\text{-}C_{12})$heteroaryl is pyridinyl, quinolinyl, or thienyl each optionally substituted with 1 substituent that is $(C_1\text{-}C_6)$alkyl or halogen; and $R^7$ is absent.

In another embodiment, the present invention provides compounds of Formula I and Formula II wherein $R^1$ is methyl; $R^2$ is methyl; $R^3$ is hydrogen; L is a bond; $R^6$ is $(C_5\text{-}C_{12})$heteroaryl, wherein the $(C_5\text{-}C_{12})$heteroaryl is pyridinyl, quinolinyl, or thienyl each optionally substituted with 1 substituent that is $(C_1\text{-}C_6)$alkyl or halogen; and $R^7$ is absent.

In another embodiment, the present invention provides compounds of Formula I and Formula II wherein $R^1$ is methyl; $R^2$ is methyl; $R^3$ is hydrogen; L is a bond, —$(CH_2)_n$—, —$(CH_2)_nO(CH_2)_p$—, —$(CH_2)_nS(CH_2)_p$—, —$(CH_2)_nNR^4(CH_2)_p$—, —$(CH_2)_nSO_2NR^4(CH_2)_p$—, —$(CH_2)_nCONR^4(CH_2)_p$—, or —$(CH_2)_nNR^4CO(CH_2)_p$—; $R^4$ and $R^5$ are independently hydrogen, $(C_1\text{-}C_6)$alkyl, or $(C_3\text{-}C_8)$cycloalkyl; n is 0, 1, or 2; p is 0, 1, or 2; $R^6$ is $(C_1\text{-}C_6)$ alkoxy$(C_1\text{-}C_6)$alkyl, $(C_1\text{-}C_6)$alkoxycarbonyl, $(C_1\text{-}C_6)$alkylthiocarbonyl, $(C_3\text{-}C_8)$cycloalkyl, hydroxy$(C_1\text{-}C_{10})$alkyl, or $(NR^4R^5)$carbonyl, wherein the $(C_3\text{-}C_8)$cycloalkyl is cyclohexyl optionally substituted with 1 substituent that is hydroxy; and $R^7$ is absent.

In another embodiment, the present invention provides compounds of Formula I and Formula II wherein $R^1$ is methyl; $R^2$ is methyl; $R^3$ is hydrogen; L is a bond, —$(CH_2)$—, —$O(CH_2)$—, —$NR^4(CH_2)$—, or —$NR^4CO$—; $R^4$ and $R^5$ are independently hydrogen, $(C_1\text{-}C_6)$alkyl, or $(C_3\text{-}C_8)$cycloalkyl; $R^6$ is $(C_1\text{-}C_6)$alkoxy$(C_1\text{-}C_6)$alkyl, $(C_1\text{-}C_6)$alkoxycarbonyl, $(C_1\text{-}C_6)$alkylthiocarbonyl, $(C_3\text{-}C_8)$cycloalkyl, hydroxy$(C_1\text{-}C_{10})$alkyl, or $(NR^4R^5)$carbonyl, wherein the $(C_3\text{-}C_8)$cycloalkyl is cyclohexyl optionally substituted with 1 substituent that is hydroxy; and $R^7$ is absent.

In another embodiment, the present invention provides pharmaceutical compositions comprising a compound of Formula I or Formula II in admixture with at least one pharmaceutically acceptable excipient.

In another embodiment, the present invention provides a method of treating bacterial infections comprising administering a therapeutically effect amount of a compound of Formula I or Formula II to a patient in need thereof.

In another embodiment, the present invention provides a use of a compound of Formula I or Formula II in the manufacture of a medicament for bacterial infections.

DEFINITIONS

As used throughout this application, including the claims, the following terms have the meanings defined below, unless specifically indicated otherwise. The plural and singular should be treated as interchangeable, other than the indication of number.

The term "$(C_2\text{-}C_6)$alkenyl" as used herein, means a straight or branched chain hydrocarbon containing from 2 to 6 carbons and containing at least one carbon-carbon double bond. Representative examples of $(C_2\text{-}C_6)$alkenyl include, but are not limited to, ethenyl, 2-propenyl, 2-methyl-2-propenyl, 3-butenyl, 4-pentenyl, and 5-hexenyl.

The term "$(C_1\text{-}C_6)$alkoxy" as used herein, means a $(C_1\text{-}C_6)$ alkyl group, as defined herein, appended to the parent molecular moiety through an oxygen atom. Representative examples of $(C_1\text{-}C_6)$alkoxy include, but are not limited to, methoxy, ethoxy, propoxy, 2-propoxy, butoxy, tert-butoxy, pentyloxy, and hexyloxy.

The term "$(C_1\text{-}C_3)$alkoxy" as used herein, means a $(C_1\text{-}C_3)$ alkyl group, as defined herein, appended to the parent molecular moiety through an oxygen atom. Examples of $(C_1\text{-}C_3)$alkoxy include methoxy, ethoxy, propoxy, and 2-propoxy (isopropoxy).

The term "$(C_1\text{-}C_6)$alkoxy$(C_1\text{-}C_6)$alkyl" as used herein, means a $(C_1\text{-}C_6)$alkoxy group, as defined herein, appended to the parent molecular moiety through a $(C_1\text{-}C_6)$alkyl group, as defined herein. Representative examples of $(C_1\text{-}C_6)$alkoxy $(C_1\text{-}C_6)$alkyl include, but are not limited to, tert-butoxymethyl, 2-ethoxyethyl, 2-methoxyethyl, and methoxymethyl.

The term "$(C_1\text{-}C_6)$alkoxycarbonyl" as used herein, means a $(C_1\text{-}C_6)$alkoxy group, as defined herein, appended to the parent molecular moiety through a carbonyl group, as defined herein. Representative examples of $(C_1\text{-}C_6)$alkoxycarbonyl include, but are not limited to, methoxycarbonyl, ethoxycarbonyl, and tert-butoxycarbonyl.

The term "$(C_1-C_6)$alkoxycarbonyl$(C_1-C_6)$alkyl" as used herein, means a $(C_1-C_6)$alkoxycarbonyl group, as defined herein, appended to the parent molecular moiety through a $(C_1-C_6)$alkyl group, as defined herein. Representative examples of $(C_1-C_6)$alkoxycarbonyl$(C_1-C_6)$alkyl include, but are not limited to, 3-methoxycarbonylpropyl, 4-ethoxycarbonylbutyl, and 2-tert-butoxycarbonylethyl.

The term "$(C_1-C_6)$alkoxysulfonyl" as used herein, means a $(C_1-C_6)$alkoxy group, as defined herein, appended appended to the parent molecular moiety through a sulfonyl group, as defined herein. Representative examples of $(C_1-C_6)$alkoxysulfonyl include, but are not limited to, methoxysulfonyl, ethoxysulfonyl and propoxysulfonyl.

The term "$(C_1-C_3)$alkyl" as used herein, means a straight or branched chain hydrocarbon containing from 1 to 3 carbon atoms. Examples of $(C_1-C_3)$alkyl include methyl, ethyl, n-propyl, and iso-propyl.

The term "$(C_1-C_6)$alkyl" as used herein, means a straight or branched chain hydrocarbon containing from 1 to 6 carbon atoms. Representative examples of $(C_1-C_6)$alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "$(C_1-C_{10})$alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "$(C_1-C_6)$alkylcarbonyl" as used herein, means a $(C_1-C_6)$alkyl group, as defined herein, appended to the parent molecular moiety through a carbonyl group, as defined herein. Representative examples of $(C_1-C_6)$alkylcarbonyl include, but are not limited to, acetyl, 1-oxopropyl, 2,2-dimethyl-1-oxopropyl, 1-oxobutyl, and 1-oxopentyl.

The term "$(C_1-C_6)$alkylcarbonyl$(C_1-C_6)$alkyl" as used herein, means a $(C_1-C_6)$alkylcarbonyl group, as defined herein, appended to the parent molecular moiety through a $(C_1-C_6)$alkyl group, as defined herein. Representative examples of $(C_1-C_6)$alkylcarbonyl$(C_1-C_6)$alkyl include, but are not limited to, 2-oxopropyl, 3,3-dimethyl-2-oxopropyl, 3-oxobutyl, and 3-oxopentyl.

The term "$(C_1-C_6)$alkylcarbonyloxy" as used herein, means a $(C_1-C_6)$alkylcarbonyl group, as defined herein, appended to the parent molecular moiety through an oxygen atom. Representative examples of $(C_1-C_6)$alkylcarbonyloxy include, but are not limited to, acetyloxy, ethylcarbonyloxy, and tert-butylcarbonyloxy.

The term "$(C_1-C_6)$alkylsulfinyl" as used herein, means an $(C_1-C_6)$alkyl group, as defined herein, appended to the parent molecular moiety through a sulfinyl group, as defined herein. Representative examples of $(C_1-C_6)$alkylsulfinyl include, but are not limited to, methylsulfinyl and ethylsulfinyl.

The term "$(C_1-C_6)$alkylsulfonyl" as used herein, means an $(C_1-C_6)$alkyl group, as defined herein, appended to the parent molecular moiety through a sulfonyl group, as defined herein. Representative examples of $(C_1-C_6)$alkylsulfonyl include, but are not limited to, methylsulfonyl and ethylsulfonyl.

The term "$(C_1-C_6)$alkylsulfonyl$(C_1-C_6)$alkyl" as used herein, means a $(C_1-C_6)$alkylsulfonyl group, as defined herein, appended to the parent molecular moiety through a $(C_1-C_6)$alkyl group, as defined herein.

The term "$(C_1-C_6)$alkylthio" as used herein, means a $(C_1-C_6)$alkyl group, as defined herein, appended to the parent molecular moiety through a sulfur atom. Representative examples of $(C_1-C_6)$alkylthio include, but are not limited to, methylthio, ethylthio, tert-butylthio, and hexylthio.

The term "$(C_1-C_6)$alkylthio$(C_1-C_6)$alkyl" as used herein, means a $(C_1-C_6)$alkylthio group, as defined herein, appended to the parent molecular moiety through a $(C_1-C_6)$alkyl group, as defined herein. Representative examples of $(C_1-C_6)$alkylthio$(C_1-C_6)$alkyl include, but are not limited to, methylthiomethyl and 2-(ethylthio)ethyl.

The term "$(C_2-C_6)$alkynyl" as used herein, means a straight or branched chain hydrocarbon group containing from 2 to 6 carbon atoms and containing at least one carbon-carbon triple bond. Representative examples of $(C_2-C_6)$alkynyl include, but are not limited to, to acetylenyl, 1-propynyl, 2-propynyl, 3-butynyl, 2-pentynyl, and 1-butynyl.

The term "$(C_6-C_{12})$aryl," as used herein, means phenyl or a bicyclic aryl. The bicyclic aryl is naphthyl, or a phenyl fused to a cycloalkyl, or a phenyl fused to a cycloalkenyl. The bicyclic aryl is attached to the parent molecular moiety through any carbon atom contained within the bicyclic aryl. Representative examples of the bicyclic aryl include, but are not limited to, dihydroindenyl, indenyl, naphthyl, dihydronaphthalenyl, and tetrahydronaphthalenyl.

The $(C_6-C_{12})$aryl groups of the invention are optionally substituted with 1, 2, 3, 4, or 5 groups that are independently $(C_2-C_6)$alkenyl, $(C_1-C_6)$alkoxy, $(C_1-C_6)$alkoxy$(C_1-C_6)$alkyl, $(C_1-C_6)$alkoxycarbonyl, $(C_1-C_6)$alkoxycarbonyl$(C_1-C_6)$alkyl, $(C_1-C_6)$alkoxysulfonyl, $(C_1-C_6)$alkyl, $(C_1-C_6)$alkylcarbonyl, $(C_1-C_6)$alkylcarbonyl$(C_1-C_6)$alkyl, $(C_1-C_6)$alkylcarbonyloxy, $(C_1-C_6)$alkylsulfinyl, $(C_1-C_6)$alkylsulfonyl, $(C_1-C_6)$alkylthio, $(C_1-C_6)$alkylthio$(C_1-C_6)$alkyl, $(C_2-C_6)$alkynyl, carboxy, carboxy$(C_1-C_6)$alkyl, cyano, cyano$(C_1-C_6)$alkyl, ethylenedioxy, formyl, halo$(C_1-C_6)$alkoxy, halo$(C_1-C_6)$alkyl, halogen, hydroxy, hydroxy$(C_1-C_6)$alkyl, mercapto, methylenedioxy, nitro, oxo, —$NZ^1Z^2$, $(NZ^1Z^2)$carbonyl, $(NZ^1Z^2)$carbonyloxy, $(NZ^1Z^2)$sulfonyl, or $(NZ^1Z^2)$sulfonyl$(C_1-C_6)$alkyl. Representative examples of substituted aryl include, but are not limited to, benzo[1,3]dioxolyl, 2,3-dihydrobenzo[1,4]dioxinyl, 2-chloro-4-methoxyphenyl, cyanophenyl, 2,3-difluorophenyl, 2,3,4,-trifluorophenyl, 2,3-dichlorophenyl, 2,6-dichlorophenyl, 2,4-dichlorophenyl, 3,4-dichlorophenyl, 2,4-difluorophenyl, 3,4-difluorophenyl, 2,6-dimethoxyphenyl, 3,4-dimethoxyphenyl, 2-fluorophenyl, 3-fluorophenyl, 4-fluorophenyl, 2-fluoro-3-methoxyphenyl, 2-fluoro-4-methoxyphenyl, 2-methoxyphenyl, 3-methoxyphenyl, 4-methoxyphenyl, 2-methylphenyl, 3-methylphenyl, 4-methyphenyl, 4-difluoromethoxy-3-methylphenyl, and 2,3,4,-trifluorophenyl.

The term "$(C_6-C_{12})$aryl$(C_1-C_6)$alkyl" as used herein, means a $(C_6-C_{12})$aryl group, as defined herein, appended to the parent molecular moiety through an $(C_1-C_6)$alkyl group, as defined herein. Representative examples of $(C_6-C_{12})$aryl$(C_1-C_6)$alkyl include, but are not limited to, benzyl, 2-phenylethyl, 3-phenylpropyl, and 2-naphth-2-ylethyl.

The term "$(C_6-C_{12})$aryl-$NR^5$—" as used herein, means a $(C_6-C_{12})$aryl group, as defined herein, appended to the parent molecular moiety through an —$NR^5$— group.

The term "$(C_6-C_{12})$aryloxy" as used herein, means a $(C_6-C_{12})$aryl group, as defined herein, appended to the parent molecular moiety through an oxygen atom. Representative examples of $(C_6-C_{12})$aryloxy include, but are not limited to, phenoxy and naphthalenyloxy.

The term "$(C_6-C_{12})$arylthio" as used herein, means a $(C_6-C_{12})$aryl group, as defined herein, appended to the parent molecular moiety through a sulfur atom. Representative examples of $(C_6-C_{12})$arylthio include, but are not limited to, phenthio and naphthalenylthio.

The term "carbonyl" as used herein, means a —C(O)— group.

The term "carboxy" as used herein, means a —CO$_2$H group.

The term "carboxy($C_1$-$C_6$)alkyl" as used herein, means a carboxy group, as defined herein, is attached to the parent molecular moiety through a ($C_1$-$C_6$)alkyl group.

The term "cyano" as used herein, means a —CN group.

The term "cyano($C_1$-$C_6$)alkyl" as used herein, means a cyano group, as defined herein, appended to the parent molecular moiety through a ($C_1$-$C_6$)alkyl group, as defined herein. Representative examples of cyanoalkyl include, but are not limited to, cyanomethyl, 2-cyanoethyl, and 3-cyanopropyl.

The term "($C_5$-$C_8$)cycloalkenyl" as used herein, means a cyclopentyl, cyclohexyl, cycloheptyl, or cyclooctyl group that contains at least one carbon-carbon double bond. Representative examples of ($C_5$-$C_8$)cycloalkenyl include, but are not limited to, cyclohexenyl, cyclohexadienyl, cyclopentenyl, cycloheptenyl, and cyclooctenyl.

The term "($C_3$-$C_8$)cycloalkyl" as used herein, means a saturated cyclic hydrocarbon group containing from 3 to 8 carbons, examples of ($C_3$-$C_8$)cycloalkyl include cyclopropyl, cyclobutyl, cyclopentyl, cyclohexyl, cycloheptyl, and cyclooctyl.

The ($C_3$-$C_8$)cycoalkyl groups of the invention are optionally substituted with 1, 2, 3, or 4 groups that are independently ($C_2$-$C_6$)alkenyl, ($C_1$-$C_6$)alkoxy, ($C_1$-$C_6$)alkoxy($C_1$-$C_6$)alkyl, ($C_1$-$C_6$)alkoxycarbonyl, ($C_1$-$C_6$)alkoxycarbonyl($C_1$-$C_6$)alkyl, ($C_1$-$C_6$)alkoxysulfonyl, ($C_1$-$C_6$)alkyl, ($C_1$-$C_6$)alkylcarbonyl, ($C_1$-$C_6$)alkylcarbonyl($C_1$-$C_6$)alkyl, ($C_1$-$C_6$)alkylcarbonyloxy, ($C_1$-$C_6$)alkylsulfinyl, ($C_1$-$C_6$)alkylsulfonyl, ($C_1$-$C_6$)alkylthio, ($C_1$-$C_6$)alkylthio($C_1$-$C_6$)alkyl, ($C_2$-$C_6$)alkynyl, carboxy, carboxy($C_1$-$C_6$)alkyl, cyano, cyano($C_1$-$C_6$)alkyl, ethylenedioxy, formyl, halo($C_1$-$C_6$)alkoxy, halo($C_1$-$C_6$)alkyl, halogen, hydroxy, hydroxy($C_1$-$C_6$)alkyl, mercapto, nitro, oxo, —NZ$^1$Z$^2$, (NZ$^1$Z$^2$)carbonyl, (NZ$^1$Z$^2$)carbonyloxy, (NZ$^1$Z$^2$)sulfonyl, or (NZ$^1$Z$^2$)sulfonyl($C_1$-$C_6$)alkyl.

The term "($C_3$-$C_8$)cycloalkyl($C_1$-$C_6$)alkyl" as used herein, means a ($C_3$-$C_8$)cycloalkyl group, as defined herein, appended to the parent molecular moiety through a ($C_1$-$C_6$) alkyl group, as defined herein. Representative examples of ($C_3$-$C_8$)cycloalkyl($C_1$-$C_6$)alkyl include, but are not limited to, cyclopropylmethyl, 2-cyclobutylethyl, cyclopentylmethyl, cyclohexylmethyl, and 4-cycloheptylbutyl.

The term "($C_3$-$C_8$)cycloalkyl-NR$^5$—" as used herein, means a ($C_3$-$C_8$)cycloalkyl group, as defined herein, appended to the parent molecular moiety through a —NR$^5$— group.

The term "($C_3$-$C_8$)cycloalkyloxy" as used herein, means a ($C_3$-$C_8$)cycloalkyl group, as defined herein, appended to the parent molecular moiety through an oxygen atom. Representative examples of ($C_3$-$C_8$)cycloalkyloxy include, but are not limited to, cyclopropyloxy, 2-cyclobutyloxy, cyclopentyloxy, cyclohexyloxy, and 4-cycloheptyloxy.

The term "($C_3$-$C_8$)cycloalkylthio" as used herein, means a ($C_3$-$C_8$)cycloalkyl group, as defined herein, appended to the parent molecular moiety through a sulfur atom. Representative examples of ($C_3$-$C_8$)cycloalkylthio include, but are not limited to, cyclopropylthio, cyclobutylthio, cyclopentylthio, cyclohexylthio, and cycloheptylthio.

The term "ethylenedioxy" as used herein, means a —O(CH$_2$)$_2$O— group wherein the oxygen atoms of the ethylenedioxy group are attached to the parent molecular moiety through one carbon atom forming a 5 membered ring or the oxygen atoms of the ethylenedioxy group are attached to the parent molecular moiety through two adjacent carbon atoms forming a six membered ring.

The term "formyl" as used herein, means a —C(O)H group.

The term "halo" or "halogen" as used herein, means —Cl, —Br, —I or —F.

The term "halo($C_1$-$C_3$)alkoxy" as used herein, means at least one halogen, as defined herein, appended to the parent molecular moiety through a ($C_1$-$C_3$)alkoxy group, as defined herein. Representative examples of halo($C_1$-$C_3$)alkoxy include, but are not limited to, chloromethoxy, 2-fluoroethoxy, trifluoromethoxy, and pentafluoroethoxy.

The term "halo($C_1$-$C_6$)alkyl" as used herein, means at least one halogen, as defined herein, appended to the parent molecular moiety through a ($C_1$-$C_6$)alkyl group, as defined herein. Representative examples of halo($C_1$-$C_6$)alkyl include, but are not limited to, chloromethyl, 2-fluoroethyl, trifluoromethyl, pentafluoroethyl, and 2-chloro-3-fluoropentyl.

The term "halo($C_1$-$C_3$)alkyl" as used herein, means at least one halogen, as defined herein, appended to the parent molecular moiety through a ($C_1$-$C_3$)alkyl group, as defined herein. Representative examples of halo($C_1$-$C_3$)alkyl include, but are not limited to, chloromethyl, difluoromethyl, 2-fluoroethyl, 2,2-difluoroethyl, trifluoromethyl, pentafluoroethyl, and 2-chloro-3-fluoropentyl.

The term "($C_5$-$C_{12}$)heteroaryl," as used herein, means a monocyclic heteroaryl or a bicyclic heteroaryl. The monocyclic heteroaryl is a 5 or 6 membered ring. The 5 membered ring consists of two double bonds and one, two, three or four nitrogen atoms and/or optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The monocyclic heteroaryl and the bicyclic heteroaryl are connected to the parent molecular moiety through any carbon atom or any nitrogen atom contained within the monocyclic heteroaryl or the bicyclic heteroaryl. Representative examples of bicyclic heteroaryl include, but are not limited to, benzimidazolyl, benzofuranyl, benzothienyl, benzoxadiazolyl, cinnolinyl, dihydroquinolinyl, dihydroisoquinolinyl, furopyridinyl, indazolyl, indolyl, isoquinolinyl, naphthyridinyl, quinolinyl, tetrahydroquinolinyl, and thienopyridinyl.

The ($C_5$-$C_{12}$)heteroaryl groups of the invention are optionally substituted with 1, 2, 3, or 4 groups that are independently ($C_1$-$C_6$)alkoxy($C_1$-$C_6$)alkyl, ($C_1$-$C_6$)alkoxycarbonyl, ($C_1$-$C_6$)alkoxycarbonyl($C_1$-$C_6$)alkyl, ($C_1$-$C_6$)alkoxysulfonyl, ($C_1$-$C_6$)alkyl, ($C_1$-$C_6$)alkylcarbonyl, ($C_1$-$C_6$)alkylcarbonyl($C_1$-$C_6$)alkyl, ($C_1$-$C_6$)alkylcarbonyloxy, ($C_1$-$C_6$)alkylsulfinyl, ($C_1$-$C_6$)alkylsulfonyl, ($C_1$-$C_6$)alkylthio, ($C_1$-$C_6$)alkylthio($C_1$-$C_6$)alkyl, ($C_2$-$C_6$)alkynyl, carboxy, carboxy($C_1$-$C_6$) alkyl, cyano, cyano($C_1$-$C_6$)alkyl, ethylenedioxy, formyl, halo ($C_1$-$C_6$)alkoxy, halo($C_1$-$C_6$)alkyl, halogen, hydroxy, hydroxy ($C_1$-$C_6$)alkyl, mercapto, nitro, —NZ$^1$Z$^2$, (NZ$^1$Z$^2$)carbonyl, (NZ$^1$Z$^2$)carbonyloxy, (NZ$^1$Z$^2$)sulfonyl, or (NZ$^1$Z$^2$)sulfonyl ($C_1$-$C_6$)alkyl. Heteroaryl groups of the invention that are substituted may be as tautomers. The present invention encompasses all tautomers including non-aromatic tautomers.

The term "($C_5$-$C_{12}$)heteroaryl($C_1$-$C_6$)alkyl" as used herein, means a ($C_5$-$C_{12}$)heteroaryl, as defined herein, appended to the parent molecular moiety through an ($C_1$-$C_6$) alkyl group, as defined herein. Representative examples of ($C_5$-$C_{12}$)heteroaryl($C_1$-$C_6$)alkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, 6-chloropyridin-3-ylmethyl, pyridin-4-ylmethyl, (6-(trifluoromethyl)pyridin-3-yl)methyl, (6-(cyano)pyridin-3-yl)methyl, (2-(cyano)pyridin-4-yl)methyl, (5-(cyano)pyridin-2-yl)methyl, (2-(chloro)pyridin-4-yl)methyl, pyrimidin-5-ylmethyl, 2-(pyrimidin-2-yl)propyl, thien-2-ylmethyl, and thien-3-ylmethyl.

The term "($C_3$-$C_{12}$)heteroaryl-$NR^5$—" as used herein, means a ($C_5$-$C_{12}$)heteroaryl, as defined herein, appended to the parent molecular moiety through a $NR^5$ group.

The term "($C_5$-$C_{12}$)heteroaryloxy" as used herein, means a ($C_5$-$C_{12}$)heteroaryl group, as defined herein, appended to the parent molecular moiety through an oxygen atom. Representative examples of ($C_5$-$C_{12}$)heteroaryloxy include, but are not limited to, fur-3-yloxy, 1H-imidazol-2-yloxy, 1H-imidazol-4-yloxy, pyridin-3-yloxy, 6-chloropyridin-3-yloxy, pyridin-4-yloxy, (6-(trifluoromethyl)pyridin-3-yl)oxy, (6-(cyano)pyridin-3-yl)oxy, (2-(cyano)pyridin-4-yl)oxy, (5-(cyano)pyridin-2-yl)oxy, (2-(chloro)pyridin-4-yl)oxy, pyrimidin-5-yloxy, pyrimidin-2-yloxy, thien-2-yloxy, and thien-3-yloxy.

The term "($C_5$-$C_{12}$)heteroarylthio" as used herein, means a ($C_5$-$C_{12}$)heteroaryl group, as defined herein, appended to the parent molecular moiety through a sulfur atom. Representative examples of ($C_5$-$C_{12}$)heteroarylthio include, but are not limited to, pyridin-3-ylthio and quinolin-3-ylthio.

The term "($C_3$-$C_{13}$)heterocycle" or "heterocyclic" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. The bicyclic heterocycle consists of a monocyclic heterocycle fused to a phenyl, or a monocyclic heterocycle fused to a cycloalkyl, or a monocyclic heterocycle fused to a cycloalkenyl. The monocyclic heterocycle and bicyclic heterocycle are connected to the parent molecular moiety through any carbon atom or any nitrogen atom contained within the heterocycle. Representative examples of ($C_5$-$C_{13}$)heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl(thiomorpholine sulfone), thiopyranyl, and trithianyl.

The ($C_3$-$C_{13}$)heterocycle groups of the invention are optionally substituted with 1, 2, 3, 4, or 5 groups that are independently independently ($C_2$-$C_6$)alkenyl, ($C_1$-$C_6$)alkoxy, ($C_1$-$C_6$)alkoxy($C_1$-$C_6$)alkyl, ($C_1$-$C_6$)alkoxycarbonyl, ($C_1$-$C_6$)alkoxycarbonyl($C_1$-$C_6$)alkyl, ($C_1$-$C_6$)alkoxysulfonyl, ($C_1$-$C_6$)alkyl, ($C_1$-$C_6$)alkylcarbonyl, ($C_1$-$C_6$)alkylcarbonyl($C_1$-$C_6$)alkyl, ($C_1$-$C_6$)alkylcarbonyloxy, ($C_1$-$C_6$)alkylsulfinyl, ($C_1$-$C_6$)alkylsulfonyl, ($C_1$-$C_6$)alkylthio, ($C_1$-$C_6$) alkylthio($C_1$-$C_6$)alkyl, ($C_2$-$C_6$)alkynyl, carboxy, carboxy ($C_1$-$C_6$)alkyl, cyano, cyano($C_1$-$C_6$)alkyl, ethylenedioxy, formyl, halo($C_1$-$C_6$)alkoxy, halo($C_1$-$C_6$)alkyl, halogen, hydroxy, hydroxy($C_1$-$C_6$)alkyl, mercapto, nitro, oxo, —$NZ^1Z^2$, ($NZ^1Z^2$)carbonyl, ($NZ^1Z^2$)carbonyloxy, ($NZ^1Z^2$) sulfonyl, or ($NZ^1Z^2$)sulfonyl($C_1$-$C_6$)alkyl.

The term "($C_3$-$C_{13}$)heterocycle($C_1$-$C_6$)alkyl" as used herein, means a ($C_5$-$C_{13}$)heterocycle, as defined herein, appended to the parent molecular moiety through an ($C_1$-$C_6$) alkyl group, as defined herein.

The term "($C_3$-$C_{13}$)heterocycle-$NR^5$—" as used herein, means a ($C_5$-$C_{13}$)heterocycle, as defined herein, appended to the parent molecular moiety through a $NR^5$ group.

The term "($C_3$-$C_{13}$)heterocycleoxy" as used herein, means a ($C_5$-$C_{13}$)heterocycle, as defined herein, appended to the parent molecular moiety through an oxygen atom.

The term "($C_3$-$C_{13}$)heterocyclethio" as used herein, means a ($C_5$-$C_{13}$)heterocycle, as defined herein, appended to the parent molecular moiety through a sulfur atom. Representative examples of heteroarylthio include, but are not limited to, pyridin-3-ylthio and quinolin-3-ylthio.

The term "hydroxy" as used herein, means an —OH group.

The term "hydroxy($C_1$-$C_{10}$)alkyl" as used herein, means at least one hydroxy group, as defined herein, is appended to the parent molecular moiety through a ($C_1$-$C_{10}$)alkyl group, as defined herein. Representative examples of hydroxy($C_1$-$C_{10}$) alkyl include, but are not limited to, hydroxymethyl, 2-hydroxyethyl, 3-hydroxypropyl, 2,3-dihydroxypentyl, 2-ethyl-4-hydroxyheptyl, 5,6-dihydroxyoctyl, and 9-hydroxynonyl.

The term "hydroxy($C_1$-$C_6$)alkylthio" as used herein, means a hydroxy($C_1$-$C_6$)alkyl group, as defined herein, is appended to the parent molecular moiety through a sulfur atom.

The term "mercapto" as used herein, means a —SH group.

The term "mercapto($C_1$-$C_{10}$)alkyl" as used herein, means at least one mercapto group, as defined herein, is appended to the parent molecular moiety through a ($C_1$-$C_{10}$)alkyl group, as defined herein.

The term "methylenedioxy" as used herein, means a —O($CH_2$)O— group wherein the oxygen atoms of the methylenedioxy group are attached to the parent molecular moiety through two adjacent carbon atoms forming a five membered ring.

The term "nitro" as used herein, means a —$NO_2$ group.

The term "$NZ^1Z^2$" as used herein, means two groups, $Z^1$ and $Z^2$, which are appended to the parent molecular moiety through a nitrogen atom. $Z^1$ and $Z^2$ are each independently hydrogen, ($C_1$-$C_6$)alkyl, ($C_1$-$C_6$)alkylcarbonyl, or formyl. Representative examples of $NZ^1Z^2$ include, but are not limited to, amino, methylamino, acetylamino, acetylmethylamino, butylamino, diethylamino, dimethylamino, ethylmethylamino, and formylamino.

The term "($NZ^1Z^2$)carbonyl" as used herein, means a $NZ^1Z^2$ group, as defined herein, appended to the parent molecular moiety through a carbonyl group, as defined herein. Representative examples of ($NZ^1Z^2$)carbonyl include, but are not limited to, aminocarbonyl, (methylamino)carbonyl, (dimethylamino)carbonyl, and (ethylmethylamino)carbonyl.

The term "$NZ^1Z^2$($C_1$-$C_6$)alkyl" as used herein, means a $NZ^1Z^2$ group, as defined herein, appended to the parent molecular moiety through a ($C_1$-$C_6$)alkyl group, as defined herein.

The term "(NZ$^1$Z$^2$)carbonyloxy" as used herein, means a (NZ$^1$Z$^2$)carbonyl group, as defined herein, appended to the parent molecular moiety through an oxygen atom.

The term "(NZ$^1$Z$^2$)sulfonyl" as used herein, means a NZ$^1$Z$^2$ group, as defined herein, appended to the parent molecular moiety through a sulfonyl group, as defined herein. Representative examples of (NZ$^1$Z$^2$)sulfonyl include, but are not limited to, aminosulfonyl, (methylamino)sulfonyl, (dimethylamino)sulfonyl, and (ethylmethylamino)sulfonyl.

The term "(NZ$^1$Z$^2$)carbonyl(C$_1$-C$_6$)alkyl" as used herein, means a (NZ$^1$Z$^2$)carbonyl group, as defined herein, appended to the parent molecular moiety through a (C$_1$-C$_6$)alkyl group, as defined herein.

The term "(NZ$^1$Z$^2$)thiocarbonyloxy" as used herein, means a (NZ$^1$Z$^2$)thiocarbonyl group, as defined herein, appended to the parent molecular moiety through an oxygen atom.

The term "oxo" as used herein, means a =O moiety.

The term "sulfinyl" as used herein, means a —S(O)— group.

The term "sulfonyl" as used herein, means a —SO$_2$— group.

The term "isomer" as used herein, means "stereoisomer" and "geometric isomer" as defined below.

The term "stereoisomer" as used herein, means compounds that possess one or more chiral centers and each center may exist in the (R) or (S) configuration. Stereoisomers include all diastereomeric, enantiomeric and epimeric forms as well as racemates and mixtures thereof.

The term "geometric isomer" as used herein, means compounds that may exist in cis, trans, anti, entgegen (E), and zusammen (Z) forms as well as mixtures thereof.

Compounds of "Formula I", "Formula II", and "compounds of the invention" are being used interchangeably throughout the application and should be treated as synonyms.

The term "patient" as used herein, means warm blooded animals such as, for example, livestock, guinea pigs, mice, rats, gerbils, cats, rabbits, dogs, monkeys, chimpanzees, and humans.

The phrase "pharmaceutically acceptable" as used herein, means that the substance or composition must be compatible chemically and/or toxicologically, with the other ingredients comprising a formulation, and/or the mammal being treated therewith.

The phrase "therapeutically effective amount" as used herein, means an amount of a compound of Formula I or Formula II that, when administered to a patient, provides the desired effect, i.e., lessening in the severity of the symptoms associated with a bacterial infection, decreasing the number of bacteria in the affected tissue, and/or preventing bacteria in the affected tissue from increasing in number (localized or systemic).

The term "treat" as used herein, means the ability of the compounds to relieve, alleviate or slow the progression of the patient's bacterial infection (or condition) or any tissue damage associated with the disease.

The phrase "pharmaceutically acceptable salt(s)" as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present invention that include a basic moiety, such as an amino group, may form pharmaceutically acceptable salts with various amino acids, in addition to the acids mentioned above.

The invention also relates to base addition salts of the compounds of the invention. The chemical bases that may be used as reagents to prepare these pharmaceutically acceptable base salts are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

Suitable base salts are formed from bases which form non-toxic salts. Non-limiting examples of suitable base salts include the aluminum, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see *Handbook of Pharmaceutical Salts: Properties, Selection, and Use* by Stahl and Wermuth (Wiley-VCH, 2002). Methods for making pharmaceutically acceptable salts of compounds of the invention are known to one of skill in the art.

Certain of the compounds of Formula I and Formula II may exist as geometric isomers. The compounds of Formula I and Formula II may possess one or more asymmetric centers, thus existing as two or more stereoisomeric forms. The present invention includes all the individual stereoisomers and geometric isomers of the compounds of Formula I and Formula II and mixtures thereof. Individual enantiomers can be obtained by chiral separation or using the relevant enantiomer in the synthesis.

In addition, the compounds of the present invention can exist in unsolvated as well as solvated forms with pharmaceutically acceptable solvents such as water, ethanol and the like. In general, the solvated forms are considered equivalent to the unsolvated forms for the purposes of the present invention. The compounds may also exist in one or more crystalline states, i.e. polymorphs, or they may exist as amorphous solids. All such forms are encompassed by the claims.

The invention also relates to prodrugs of the compounds of the invention. Thus certain derivatives of compounds of the invention which may have little or no pharmacological activity themselves can, when administered into or onto the body, be converted into compounds of the invention having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

This invention also encompasses compounds of the invention containing protective groups. One skilled in the art will also appreciate that compounds of the invention can also be prepared with certain protecting groups that are useful for purification or storage and can be removed before administration to a patient. The protection and deprotection of functional groups is described in "Protective Groups in Organic Chemistry", edited by J. W. F. McOmie, Plenum Press (1973) and "Protective Groups in Organic Synthesis", 3rd edition, T. W. Greene and P. G. M. Wuts, Wiley-Interscience (1999).

The present invention also includes isotopically-labeled compounds, which are identical to those recited in Formula I and Formula II, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as, but not limited to, $^2H$, $^3H$, $^{13}C$, $^{14}C$, $^{15}N$, $^{17}O$, $^{18}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically-labeled compounds of this invention and prodrugs thereof can generally be prepared by carrying out the procedures disclosed in the Schemes and/or in the Examples below, by substituting a readily available isotopically-labeled reagent for a non-isotopically-labeled reagent.

All of the compounds of Formula I and Formula II contain a sulfonyl moiety as depicted below:

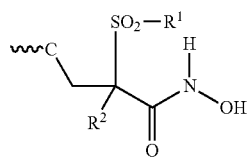

This sulfonyl moiety will always be substituted with a lower alkyl moiety. Typically, it will be methyl. The carbon atom adjacent to the sulfonyl may optionally be substituted, as represented by $R^2$. Typically, both $R^1$ and $R^2$ will be methyl.

As is readily apparent to one skilled in the art, the carbon adjacent to the sulfonyl moiety is a chiral center. Therefore, the compounds can exist as the racemate, as the (S) enantiomer, or as the (R) enantiomer. In a further embodiment, the compounds may be prepared and administered as the (R) enantiomer, as depicted below:

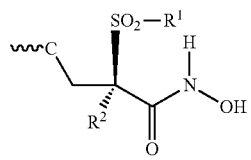

As is readily apparent to one skilled in the art, the compounds as synthesized will rarely be present exclusively as a single enantiomer. The opposite enantiomer (i.e., the (S) enantiomer) may be present in minor amounts (i.e., "substantially pure"). This minor amount can be up to 10 w/w %, more typically no greater than 5 w/w %, in a further embodiment no greater than 1 w/w %, or more specifically, no greater than 0.5 w/w %.

Synthesis

The compounds of Formula I and Formula II can be prepared by a variety of methods that are analogously known in the art. The reaction schemes presented below illustrate two general methods for the preparation of these compounds. Other methods, including modifications thereof, will be readily apparent to those skilled in the art.

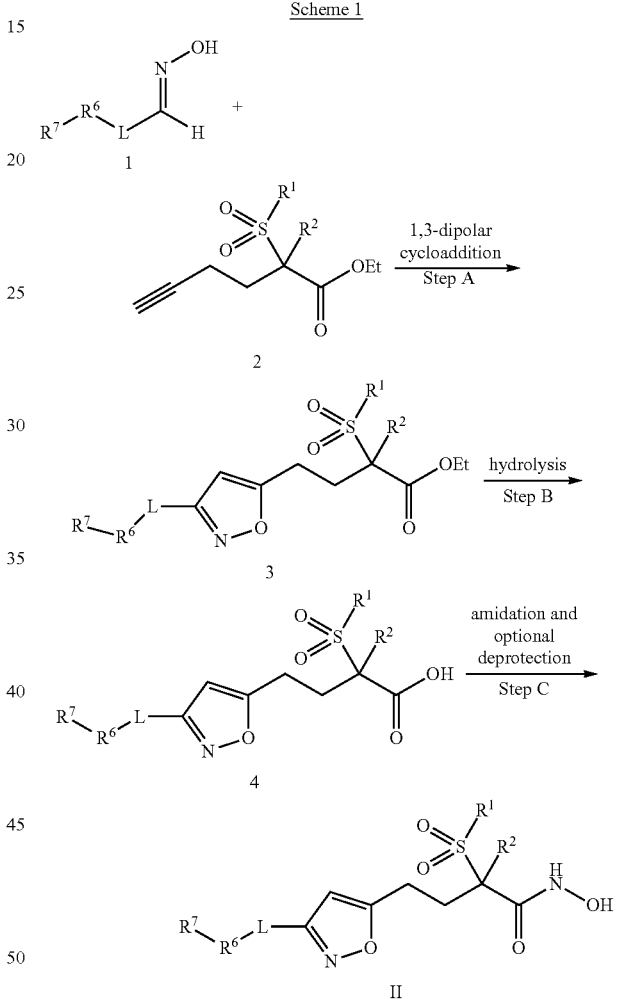

Scheme 1 illustrates the general preparation of the compounds of Formula II, where the initial step (Step A) involves the construction of an isoxazole 3, where $R^1$, $R^2$, $R^6$, $R^7$, and L are as defined in Formula II in the Summary section herein. The starting materials are the aldoxime derivative of structure 1 and the alkynyl sulfone of structure 2. Many of these aldoximes 1 are known, are commercially available, and/or can be prepared using standard synthetic techniques. The alkynyl sulfone 2 is prepared using standard synthetic techniques and methods by those skilled in the art. $R^1$, $R^2$, $R^6$, $R^7$, and L represent the same moiety as is desired in the final product. An ethyl protecting group of the carboxylic acid (an ethyl ester) is depicted, but any standard protecting group as described in J. Org. Chem. (1980) Vol. 45, 1486 and "Preparation 1."

In Step A, a nitrile oxide, generated in situ by the oxidation dehydrogenation of an aldoxime 1, undergoes a 1,3-dipolar cycloaddition with alkyne 2 in a similar manner as described in Synthesis (1982) Vol. 6, 508. Typically, an equivalent amount of the aldoxime and alkyne is mixed together in the presence of an oxidant such as sodium hypochlorite to afford the isoxazole. A variety of oxidants, solvent systems, temperatures, and protocols may be employed for this reaction, and the desired product is isolated and purified using standard techniques.

In Step B, a carboxylic acid 4 is liberated. Typically, this is achieved by a basic hydrolysis of the ester, however, the manner in which this is accomplished will vary with the identity of the protecting group and is well-known to those skilled in the art.

In Step C, the hydroxamic acid moiety, as depicted, is incorporated into the molecule. Typically, a protected hydroxylamine is used in a standard amidation reaction to provide the protected hydroxamic acid, which is then subjected the appropriate deprotection conditions to provide the desired hydroxamic acid. In some cases, the deprotection may occur under the reaction conditions for the amidation reaction. In either case, the protected intermediate and/or the desired final product is isolated from the reaction medium and purified using techniques known in the art.

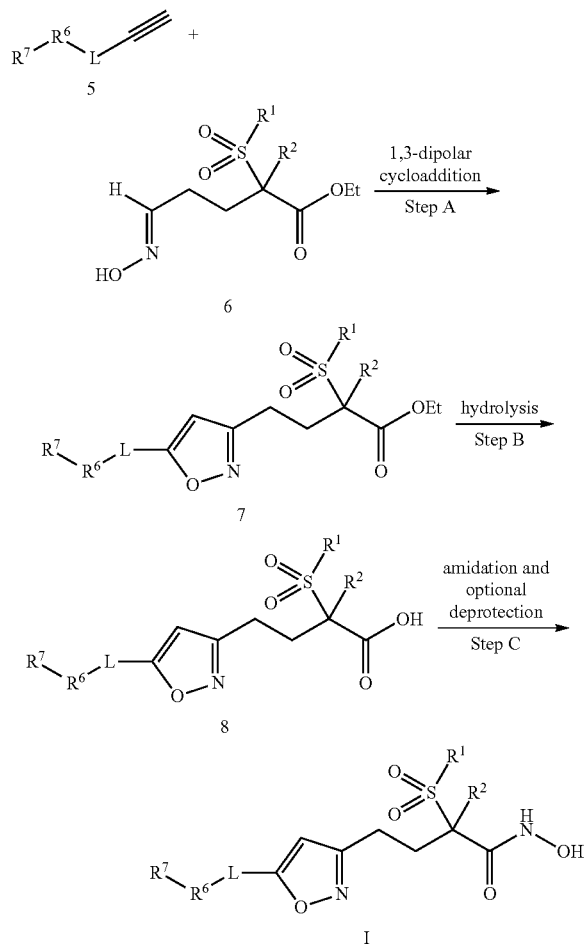

Scheme 2

Scheme 2 illustrates the general preparation of the compounds of Formula I, which follows the same sequence of reactions (Steps A-C) for the preparation of the compounds of Formula II, where $R^1$, $R^2$, $R^6$, $R^7$, and L are as defined in Formula II in the Summary section herein. Since the steps are analogous, those skilled in the art will be able to prepare the compounds of Formula I by referring to the description of Scheme 1. The starting materials are the alkyne derivative of structure 5 and the aldoxime sulfone of structure 6, and they produce the isoxazole 7, a regioisomer of structure 3 (Scheme 1), in the 1,3-dipolar cycloaddition (Scheme 2). Many of these alkynes 5 are known, are commercially available, and/or may be prepared using standard synthetic techniques. The aldoxime sulfone 6 may be prepared using standard synthetic techniques and methods. $R^1$, $R^2$, $R^6$, $R^7$, and L represent the same moiety as is desired in the final product. An ethyl protecting group of the carboxylic acid (an ethyl ester) is depicted, but any standard protecting group as described in *J. Org. Chem.* (1980) Vol. 45, 1486, "Preparation 2," and "Preparation 3."

Medical and Veterinary Uses

The compounds may be used for the treatment or prevention of infectious disorders, especially those caused by susceptible and multi-drug resistant (MDR) Gram-negative bacteria. Examples of such Gram-negative bacteria include *Acinetobacter baumannii*, *Acinetobacter* spp., *Achromobacter* spp., *Aeromonas* spp., *Bacteroides fragilis*, *Bordetella* spp., *Borrelia* spp., *Brucella* spp., *Campylobacter* spp., *Citrobacter diversus* (koseri), *Citrobacter freundii*, *Enterobacter aerogenes*, *Enterobacter cloacae*, *Escherichia coli*, *Francisella tularensis*, *Fusobacterium* spp., *Haemophilus influenzae* (β-lactamase positive and negative), *Helicobacter pylori*, *Klebsiella oxytoca*, *Klebsiella pneumoniae* (including those encoding extended-spectrum β-lactamases (hereinafter "ESBLs"), *Legionella pneumophila*, *Moraxella catarrhalis* (β-lactamase positive and negative), *Morganella morganii*, *Neisseria gonorrhoeae*, *Neisseria meningitidis*, *Proteus vulgaris*, *Porphyromonas* spp., *Prevotella* spp., *Mannheimia haemolyticus*, *Pasteurella* spp., *Proteus mirabilis*, *Providencia* spp., *Pseudomonas aeruginosa*, *Pseudomonas* spp., *Salmonella* spp., *Shigella* spp., *Serratia marcescens*, *Treponema* spp., *Burkholderia cepacia*, *Vibrio* spp., *Yersinia* spp., and *Stenotrophomonas maftophilia*. Examples of other Gram-negative organisms include members of the Enterobacteriaceae that express ESBLs; KPCs, CTX-M, metallo-β-lactamases (such as NDM-1, for example), and AmpC-type beta-lactamases that confer resistance to currently available cephalosporins, cephamycins, carbapenems, beta-lactams, and beta-lactam/beta-lactamase inhibitor combinations.

In a more specific embodiment, the Gram-negative bacteria are selected from the group consisting of *Acinetobacter baumannii*, *Acinetobacter* spp., *Citrobacter* spp., *Enterobacter aerogenes*, *Enterobacter cloacae*, *Escherichia coli*, *Klebsiella oxytoca*, *Klebsiella pneumoniae*, *Serratia marcescens*, *Stenotrophomonas maltophilia*, *Pseudomonas aeruginosa* and members of the Enterobacteriaceae and *Pseudomonas* that express ESBLs, KPCs, CTX-M, metallo-β-lactamases, and AmpC-type beta-lactamases that confer resistance to currently available cephalosporins, cephamycins, carbapenems, beta-lactams, and beta-lactam/beta-lactamase inhibitor combinations.

Examples of infections that may be treated with the compounds of Formula I and Formula II include nosocomial pneumonia, urinary tract infections, systemic infections (bacteremia and sepsis), skin and soft tissue infections, surgical infections, intraabdominal infections, lung infections in patients with cystic fibrosis, patients suffering from lung infections, endocarditis, diabetic foot infections, osteomyelitis, and central nervous system infections.

In addition, the compounds can be used to treat *Helicobacter pylori* infections in the GI tract of humans (and other mammals). Elimination of these bacteria is associated with improved health outcomes including fewer dyspeptic symptoms, reduced peptic ulcer recurrence and rebleeding, reduced risk of gastric cancer, etc. A more detailed discussion of eradicating *H. pylori* and its impact on gastrointestinal illness may be found at: www.informahealthcare.com, Expert Opin. Drug Saf. (2008) 7(3).

In order to exhibit this anti-infective activity, the compounds need to be administered in a therapeutically effective amount. A "therapeutically effective amount" is meant to describe a sufficient quantity of the compound to treat the infection, at a reasonable benefit/risk ratio applicable to any such medical treatment. It will be understood, however, that the attending physician, within the scope of sound medical judgment, will decide the total daily dosage of the compound. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. As a general guideline however, the total daily dose will typically range from about 0.1 mg/kg/day to about 5000 mg/kg/day in single or in divided doses. Typically, dosages for humans will range from about 10 mg to about 3000 mg per day, in a single or multiple doses.

Any route typically used to treat infectious illnesses, including oral, parenteral, topical, rectal, transmucosal, and intestinal, can be used to administer the compounds. Parenteral administrations include injections to generate a systemic effect or injections directly into to the afflicted area. Examples of parenteral administrations are subcutaneous, intravenous, intramuscular, intradermal, intrathecal, and intraocular, intranasal, intravetricular injections or infusions techniques. Topical administrations include the treatment of areas readily accessible by local application, such as, for example, eyes, ears including external and middle ear infections, vaginal, open wound, skin including the surface skin and the underneath dermal structures, or lower intestinal tract. Transmucosal administration includes nasal aerosol or inhalation applications.

Formulations

Compounds of the invention can be formulated for administration in any way for use in human or veterinary medicine, by analogy with other bioactive agents such as antibiotics. Such methods are known in the art and are summarized below.

The composition can be formulated for administration by any route known in the art, such as subdermal, by-inhalation, oral, topical or parenteral. The compositions may be in any form known in the art, including but not limited to tablets, capsules, powders, granules, lozenges, creams or liquid preparations, such as oral or sterile parenteral solutions or suspensions.

The topical formulations of the present invention can be presented as, for instance, ointments, creams or lotions, ophthalmic ointments/drops and otic drops, impregnated dressings and aerosols, and may contain appropriate conventional additives such as preservatives, solvents to assist drug penetration and emollients, etc. Such topical formulations may also contain conventional carriers, such as cream or ointment bases and ethanol or oleyl alcohol for lotions. Such carriers may be present, for example, from about 1% up to about 98% of the formulation.

Tablets and capsules for oral administration may be in unit dose presentation form, and may contain conventional excipients such as binding agents, for example, acacia, gelatin, sorbitol, tragacanth, or polyvinylpyrollidone; fillers, for example lactose, sugar, maize-starch, calcium phosphate, sorbitol or glycine; tabletting lubricants, for example, magnesium stearate, talc, polyethylene glycol or silica; disintegrants, for example, potato starch; or acceptable wetting agents such as sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example, sorbitol, methyl cellulose, glucose syrup, gelatin, hydroxyethyl cellulose, carboxymethyl cellulose, aluminium stearate gel or hydrogenated edible fats, emulsifying agents, for example, lecithin, sorbitan monooleate, or acacia; non-aqueous vehicles (which may include edible oils), for example, almond oil, oily esters such as glycerin, propylene glycol, or ethyl alcohol; preservatives, for example, methyl or propyl p-hydroxybenzoate or sorbic acid; and, if desired, conventional flavoring or coloring agents.

For parenteral administration, fluid unit dosage forms are prepared utilizing the compound and a sterile vehicle, water being typical. The compound, depending on the vehicle and concentration used, can be either suspended or dissolved in the vehicle or other suitable solvent. In preparing solutions, the compound can be dissolved in water for injection and filter sterilized before filling into a suitable vial or ampoule and sealing. Advantageously, agents such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain, for example, from about 0.1% by weight, to about 100% by weight, of the active material, depending on the method of administration. Where the compositions comprise dosage units, each unit will contain, for example, from about 0.5-1000 mg of the active ingredient. The dosage as employed for adult human treatment will range, for example, from about 10 to 3000 mg per day, depending on the route and frequency of administration.

If desired, the compounds of the invention may be administered in combination with one or more additional antibacterial agents ("the additional active agent"). Such use of compounds of the invention in combination with an additional active agent may be for simultaneous, separate or sequential use.

The Examples and preparations provided below further illustrate and exemplify the compounds of the present invention and methods of preparing such compounds. It is to be understood that the scope of the present invention is not limited in any way by the scope of the following Examples and preparations. In the following Examples, molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXPERIMENTAL PROCEDURES

Experiments were generally carried out under an inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Company, Milwaukee, Wis.). Mass spectrometry data is reported from either liquid chromatography-mass spectrometry (LCMS) or atmospheric pressure chemical ionization (APCI). Chemical shifts for nuclear magnetic resonance (NMR) data are expressed in parts per million (ppm, δ) referenced to residual peaks from the deuterated solvents employed. Melting points are uncorrected. Low Resolution Mass Spectra (LRMS) were recorded on either a Hewlett Packard 5989®, utilizing chemical ionization (ammonium), or a Fisons (or Micro Mass) Atmospheric Pressure Chemical Ionization (APCI) platform which uses a 50/50 mixture of acetonitrile/water with 0.1% formic acid as the ionizing agent. Room or ambient temperature refers to 20-25° C.

For syntheses referencing procedures in other Examples, reaction conditions (length of reaction and temperature) may vary. In general, reactions were followed by thin layer chromatography or mass spectrometry, and subjected to work-up when appropriate. Purifications may vary between experiments: in general, solvents and the solvent ratios used for eluants/gradients were chosen to provide appropriate $R_f$s or retention times.

In the discussion above and in the Examples below, the following abbreviations have the following meanings. If an abbreviation is not defined, it has its generally accepted meaning.

aq.=aqueous
bm=broad multiplet
bd=broad doublet
bs=broad singlet
d=doublet
dd=doublet of doublets
dq=doublet of quartets
dt=doublet of triplets
DIAD=diisopropyl azocarboxylate
DMF=dimethylformamide
DMSO=dimethyl sulfoxide
equiv.=equivalents
g=grams
h=hours
HPLC=high pressure liquid chromatography
m=multiplet
M=molar
mg=milligram
mL=milliliter
mm=millimeter
mmol=millimol
q=quartet
s=singlet
t or tr=triplet
T3P®=2,4,6-tripropyl-1,3,5,2,4,6-trioxatriphosphinane 2,4,6-trioxide
TBS=tert-butyldimethylsilyl
TFA=trifluoroacetic acid
THF=tetrahydrofuran
TLC=thin layer chromatography
MeOH=methanol
DCM=dichloromethane
HCl=hydrochloric acid
MS=mass spectrometry
rt=room temperature
EtOAc=ethyl acetate
EtO=ethoxy
μL=microliter
J=coupling constant
NMR=nuclear magnetic resonance
MHz=megahertz
Hz=hertz
m/z=mass to charge ratio
min=minutes
H2N—OTHP=O-tetrahydro-2H-pyran-2-yl-hydroxylamine
Et$_2$O=diethyl ether
sat.=saturated Preparation of Starting Materials Preparation 1

Ethyl 2-methyl-2-(methylsulfonyl)hex-5-ynoate and individual enantiomers (R) and (S)

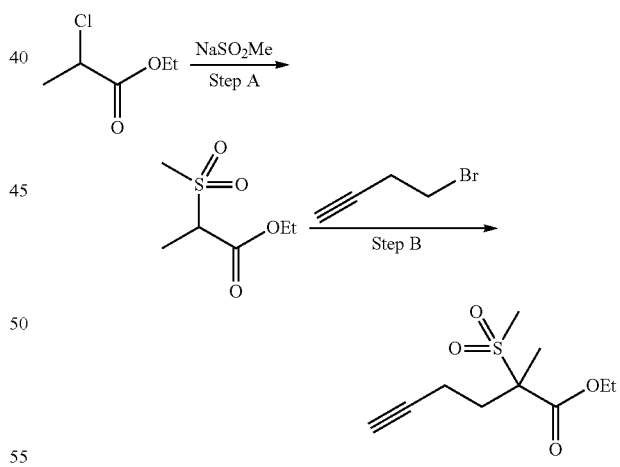

Step A)

Ethyl 2-(methylsulfonyl)propanoate

Sodium methyl sulfinate (103 g, 937 mmol) was combined with the ethyl 2-chloropropionate (109 g, 892 mmol) in ethanol (350 mL) in a 500 mL one neck round bottom flask. The reaction was heated to 77° C. for 20 h, and then allowed to cool to room temperature. Solids were removed by filtration through celite, and the filter pad was washed with ethanol. The combined filtrates were concentrated under reduced pressure. The crude product was suspended in diethyl ether (250 mL), and solids were removed by filtration. The filtrate was concentrated under reduced pressure to afford the title compound as a pale yellow oil (51 g, 73%). $^1$H NMR (400 MHz, CHLOROFORM-d) δ1.32 (t, J=7.05 Hz, 3H) 1.67 (d, J=7.47 Hz, 3H) 3.05 (s, 3H) 3.83-3.92 (m, 1H) 4.18-4.37 (m, 2H).

Step B)

Ethyl 2-methyl-2-(methylsulfonyl)hex-5-ynoate

Sodium hydride (60% dispersion in mineral oil, 3.9 g, 17.2 mmol, 1.2 equiv) was added to a solution of ethyl 2-(methylsulfonyl)propanoate (14.8 g, 82.0 mmol, 1.0 equiv) in N,N-dimethylformamide (180 mL) at room temperature. After the evolution of gas subsided (approx. 30 min), a stirred mixture of potassium iodide (2.89 g, 17.2 mmol, 0.2 equiv) and 4-bromobut-1-yne (10.9 g, 82.0 mmol, 1.0 equiv) in N,N-dimethylformamide (20 mL) was added dropwise via cannula (approx. 2 h). After 3 h, the reaction was quenched with water (200 mL), and the resulting solution was extracted with 1:1 ethyl acetate-hexanes (2×200 mL). The combined organic phases were washed with water (2×50 mL), brine (50 mL), dried over anhydrous magnesium sulfate, filtered and concentrated under reduced pressure. The crude material was purified by flash chromatography (340 g silica gel column, 0-25% gradient ethyl acetate in hexanes) to provide the title compound as a clear colorless oil (6.63 g, 35%). MS (GCMS) m/z 233 (M+1). $^1$H NMR (400 MHz, CHLOROFORM-d) δ1.33 (t, J=7.12 Hz, 3H) 1.64 (s, 3H) 2.00 (t, J=2.63 Hz, 1H) 2.11-2.22 (m, 1H) 2.22-2.32 (m, 1H) 2.33-2.45 (m, 1H) 2.46-2.58 (m, 1H) 3.05 (s, 3H) 4.28 (q, J=7.16 Hz, 2H).

Chiral separation of ethyl 2-methyl-2-(methylsulfonyl)hex-5-ynoate

The racemic material (20.0 g) was resolved using flash chromatography under the conditions presented in Table 1 (below) to provide enantiomer 1 (5.7 g, $[\alpha]_{589}^{20}$=+15.5°, 99% enantiomeric purity) and enantiomer 2 (4.7 g, $[\alpha]_{589}^{20}$=−14.7°, 99% enantiomeric purity). Enantiomer 1 was determined to be ethyl(2R)-2-methyl-2-(methylsulfonyl)hex-5-ynoate.

TABLE 1

| Prep Instrument | MultigramIII-1 |
| --- | --- |
| Column | Chiralpak AD-H |
| Dimensions | 30 mm × 250 mm |
| Mobile Phase | 95:5 CO$_2$-Methanol |
| Modifier | None |
| Flow rate | 120 g/min |
| Back Pressure | 100 Bar |
| Wavelength | 210 nm |
| Dissolving Solvent | Methanol |
| Sample Volume | 500 mL |
| Sample Concentration | 22.0 mg/mL |
| Injection Volume | 1.0 mL |
| Loading | 22.0 mg |
| Loading Rate | 0.264 g/hour |
| Injection Interval | 5 min |

Preparation 2

Ethyl 5-(hydroxyimino)-2-methyl-2-(methylsulfonyl)pentanoate and individual enantiomers (R) and (S)

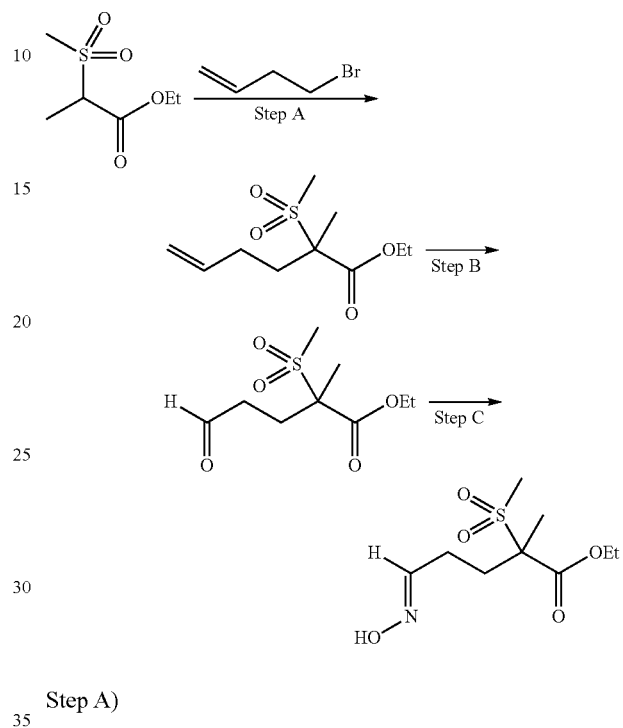

Step A)

Ethyl 2-methyl-2-(methylsulfonyl)hex-5-enoate

The title compound (8.0 g, 46%) was prepared from ethyl 2-(methylsulfonyl)propanoate (13.3 g, 74.1 mmol) and 4-bromobut-1-ene (10.0 g, 74.1 mmol) by following the procedure described for the synthesis of ethyl 2-methyl-2-(methylsulfonyl)hex-5-ynoate (Preparation 1, Step B). MS (GCMS) m/z 235 (M+1). $^1$H NMR (400 MHz, CHLOROFORM-d) δ1.33 (t, J=7.17 Hz, 3H) 1.63 (s, 3H) 1.91-2.08 (m, 2H) 2.13-2.29 (m, 1H) 2.32 (d, J=7.51 Hz, 1H) 3.05 (s, 3H) 4.29 (q, J=7.06 Hz, 2H) 4.95-5.16 (m, 2H) 5.67-5.93 (m, 1H)

Chiral separation of ethyl-2-methyl-2-(methylsulfonyl)hex-5-enoate

The racemic material (12.2 g) was resolved using flash chromatography under the conditions presented in Table 2 (below) to provide enantiomer 1 (4.2 g, $[\alpha]_{589}^{20}$=−3.7°, 99% enantiomeric purity) and enantiomer 2 (4.9 g, $[\alpha]_{589}^{20}$=+2.9°, 99% enantiomeric purity). Enantiomer 2 was determined to be ethyl(2R)-2-methyl-2-(methylsulfonyl)hex-5-enoate.

TABLE 2

| Prep Instrument | MultigramIII-1 |
| --- | --- |
| Column | Chiralpak AS-H |
| Dimensions | 30 mm × 250 mm |
| Mobile Phase | 95:5 CO$_2$-Propanol |
| Modifier | None |
| Flow rate | 120 g/min |
| Back Pressure | 100 Bar |
| Wavelength | 210 nm |
| Dissolving Solvent | Propanol |

TABLE 2-continued

| | |
|---|---|
| Sample Volume | 300 mL |
| Sample Concentration | 22.0 mg/mL |
| Injection Volume | 2.0 mL |
| Loading | 53.33 mg |
| Loading Rate | 0.961 g/hour |
| Injection Interval | 3.33 min |

Step B)

Ethyl 2-methyl-2-(methylsulfonyl)-5-oxopentanoate 2,6-Dimethylpyridine (6.1 mL, 52.9 mmol, 2.0 equiv), osmium tetroxide (2.5% w/v solution in tert-butyl alcohol, 6.6 mL, 0.53 mmol, 0.02 equiv), and sodium periodate (23.1 g, 106 mmol 4.0 equiv) were added sequentially to a solution of ethyl 2-methyl-2-(methylsulfonyl)hex-5-enoate (6.2 g, 26.0 mmol, 1.0 equiv) in 1,4-dioxane-water (3:1, 0.27 L) at room temperature. After vigorously stirring overnight (approx. 18 h), the reaction was partitioned between dichloromethane (0.2 L) and water (0.2 L). The aqueous phase was extracted with dichloromethane (0.2 L). The combined organic phases were washed with brine (30 mL), dried over anhydrous magnesium sulfate, and concentrated under reduced pressure to provide the title compound as an oil (6.2 g). MS (GCMS) m/z 237 (M+1). $^1$H NMR (400 MHz, CHLOROFORM-d) δ1.34 (t, J=7.22 Hz, 3H) 1.63 (s, 3H) 2.21-2.39 (m, 1H) 2.56 (s, 2H) 2.65-2.81 (m, 1H) 3.05-3.17 (m, 3H) 4.30 (q, J=7.15 Hz, 2H) 9.79 (s, 1H).

Step C)

Ethyl 5-(hydroxyimino)-2-methyl-2-(methylsulfonyl)pentanoate

Sodium bicarbonate (2.29 g, 27.3 mmol, 1.05 equiv) was added to a solution of hydroxylamine hydrochloride (1.94 g, 27.3 mmol, 1.05 equiv) in water (100 mL) at room temperature. After the evolution of gas ceased (approx. 30 min), a solution of ethyl 2-methyl-2-(methylsulfonyl)-5-oxopentanoate (6.14 g, 26.0 mmol, 1.0 equiv) in ethanol (100 mL) was added dropwise over 30 min, and the reaction was allowed to stir overnight (approx. 15 h). The reaction mixture was concentrated under reduced pressure to half the volume (approx. 100 mL) and partitioned between dichloromethane (200 mL) and water (100 mL). The aqueous phase was extracted with dichloromethane (100 mL). The combined organic phases were dried over anhydrous magnesium sulfate and concentrated under reduced pressure to provide the title compound (6.4 g, 97%, approx. 1:1 mixture of E/Z isomers). MS (LCMS) m/z 252.1 (M+1). $^1$H NMR (400 MHz, CHLOROFORM-d) δ1.34 (td, J=7.12, 1.17 Hz, 6H) 1.56-1.72 (m, 6H) 2.11-2.19 (m, 2H) 2.19-2.29 (m, 1H) 2.44 (d, J=3.71 Hz, 4H) 2.51-2.63 (m, 1H) 3.06 (d, J=2.93 Hz, 6H) 4.30 (qd, J=7.12, 3.22 Hz, 4H) 6.66-6.88 (m, 1H) 7.43 (d, J=5.07 Hz, 1H).

Preparation 3

1-Ethynyl-2-fluoro-3-methoxybenzene

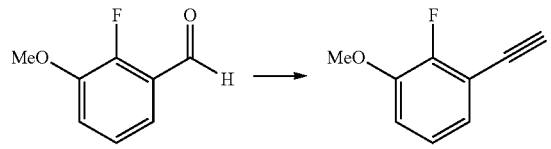

Potassium carbonate (3.6 g, 26.0 mmol) and dimethyl-1-diazo-2-oxopropylphosphonate (2.4 mL, 15.6 mmol) were added sequentially to a solution of 2-fluoro-3-methoxybenzaldehyde (2.0 g, 13.0 mmol) in methanol (100 mL), and the reaction was allowed to stir at room temperature for 16 h. After concentrating the reaction mixture under reduced pressure, the crude material was purified by flash chromatography (40 g silica gel column, 0-40% gradient ethyl acetate in hexanes) to provide a clear colorless oil (1.8 g, 92%). MS (GCMS) m/z 150. $^1$H NMR (400 MHz, CHLOROFORM-d) δ3.31 (d, J=0.78 Hz, 1H) 3.90 (s, 3H) 6.93-7.11 (m, 3H).

Example 1

(2R)-4-[3-(2-Fluoro-3-methoxyphenyl)isoxazol-5-yl]-N-hydroxy-2-methyl-2-(methylsulfonyl)butanamide

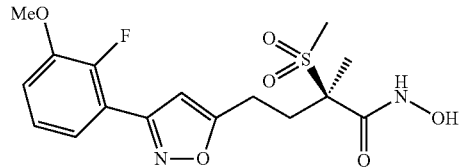 [SMILES: COc1cccc(-c2cc(CC[C@](C)(C(=O)NO)S(C)(=O)=O)on2)c1F]

Step A)

Ethyl(2R)-4-[3-(2-fluoro-3-methoxyphenyl)isoxazol-5-yl]-2-methyl-2-(methylsulfonyl)butanoate Sodium hypochlorite (6% aqueous solution, 5.7 mL, 4.6 mmol, 2.0 equiv) was added dropwise over 20 min to a cooled (0-5° C.) and vigorously stirred solution of 2-fluoro-3-methoxybenzaldehyde oxime (0.39 g, 2.3 mmol, 1.0 equiv) and ethyl(2R)-2-methyl-2-(methylsulfonyl)hex-5-ynoate (0.53 g, 2.3 mmol, 1.0 equiv) in dichloromethane (30 mL). The biphasic mixture was allowed to vigorously stir overnight (15 h) at room temperature. Water (20 mL) was added, and the mixture was extracted with dichloromethane (3×50 mL). The combined organic phases were dried over anhydrous magnesium sulfate, filtered and concentrated under reduced pressure. The crude material was purified by flash chromatography (25 g silica gel column, 0-90% gradient ethyl acetate in hexanes) to provide a clear colorless oil (0.49 g, 53%). MS (LCMS) m/z 400.1 (M+1). $^1$H NMR (400 MHz, CHLOROFORM-d) δ1.35 (t, J=7.12 Hz, 3H) 1.72 (s, 3H) 2.29-2.47 (m, 1H) 2.60-2.76 (m, 1H) 2.80-2.94 (m, 1H) 2.98 (s, 1H) 3.09 (s, 3H) 3.86-3.99 (m, 3H) 4.30 (q, J=7.09 Hz, 2H) 6.52 (d, J=3.71 Hz, 1H) 7.05 (d, J=1.56 Hz, 1H) 7.11-7.22 (m, 1H) 7.51 (s, 1H).

Step B)

(2R)-4-[3-(2-Fluoro-3-methoxyphenyl)isoxazol-5-yl]-2-methyl-2-(methylsulfonyl)butanoic acid Sodium hydroxide (1.0 M aqueous solution, 4.7 mL, 4.7 mmol, 4.0 equiv) was added to solution of ethyl(2R)-4-[3-(2-fluoro-3-methoxyphenyl)isoxazol-5-yl]-2-methyl-2-(methylsulfonyl)butanoate (0.47 g, 1.2 mmol, 1.0 equiv) in 1,4-dioxane (10 mL), and the reaction was allowed to stir overnight (18 h) at room temperature. Water (5 mL) was added, and the mixture was extracted with diethyl ether (25 mL). The aqueous phase was acidified to pH=3 with 1.0 M hydrochloric acid and then extracted with ethyl acetate (2×50 mL). The combined ethyl acetate phases were dried over potassium carbonate, filtered and concentrated under reduced pressure to provide a light tan solid (0.42 g, 96%). MS (LCMS) m/z 372.1 (M+1). $^1$H NMR (400 MHz, METHO- NAL-d$_4$) δ1.68 (s, 3H) 2.26-2.41 (m, 1H) 2.61-2.74 (m, 1H) 2.85-3.00 (m, 1H) 3.04-3.15 (m, 1H) 3.16 (s, 3H) 3.92 (s, 3H) 6.65 (d, J=3.12 Hz, 1H) 7.18-7.24 (m, 2H) 7.36-7.44 (m, 1H).

Step C)

(2R)-4-[3-(2-Fluoro-3-methoxyphenyl)isoxazol-5-yl]-N-hydroxy-2-methyl-2-(methylsulfonyl)butanamide N,N-Dimethy-4-aminopyridine (0.04 g, 0.3 mmol, 0.3 equiv), N-ethyl-N-isopropylpropan-2-amine (0.89 mL, 5.2 mmol, 4.5 equiv), T3P® (50% w/w solution in ethyl acetate, 2.7 mL, 4.5 mmol, 4.0 equiv), and (2R)-4-[3-(2-fluoro-3-methoxyphenyl)isoxazol-5-yl]-2-methyl-2-(methylsulfonyl)butanoic acid (0.42 g, 1.1 mmol, 1.0 equiv) were allowed to stir at room temperature for 30 min. A solution of O-(tetrahydro-2H-pyran-2-yl)hydroxylamine (0.15 g, 1.2 mmol, 1.2 equiv) in ethyl acetate (12 mL) was added, and the reaction was allowed to stir overnight (18 h) at room temperature. Water (40 mL) was added, and the mixture was extracted with ethyl acetate (2×50 mL). The combined organic phases were dried over anhydrous magnesium sulfate, filtered and concentrated under reduced pressure. The crude material was purified by flash chromatography (25 g silica gel column, 0-100% gradient ethyl acetate in hexanes) to provide (2R)-4-[3-(2-fluoro-3-methoxyphenyl)isoxazol-5-yl]-2-methyl-2-(methylsulfonyl)-N-(tetrahydro-2H-pyran-2-yloxy)butanamide as a tan solid (0.23 g, 42%). MS (LCMS) m/z 469.1 (M−1).

Hydrochloric acid (4.0 M in 1,4-dioxane, 0.49 mL, 1.9 mmol, 4.0 equiv) was added to a solution of (2R)-4-[3-(2-fluoro-3-methoxyphenyl)isoxazol-5-yl]-2-methyl-2-(methylsulfonyl)-N-(tetrahydro-2H-pyran-2-yloxy)butanamide (0.23 g, 0.49 mmol, 1.0 equiv) in 1,4-dioxane-dichloromethane-water (2:2:1, 5 mL), and the reaction was allowed to stir at room temperature for 2 h. The solvent was removed under reduced pressure, and the resulting crude material was purified by flash chromatography (30 g C18 reverse phase column, 5-60% gradient acetonitrile in water) to provide (2R)-4-[3-(2-fluoro-3-methoxyphenyl)isoxazol-5-yl]-N-hydroxy-2-methyl-2-(methylsulfonyl)butanamide as a light brown solid (0.09 g, 48%). MS (LCMS) m/z 387.1 (M+1). $^1$H NMR (400 MHz, METHONAL-d$_4$) δ1.67 (s, 3H) 2.20-2.38 (m, 1H) 2.80 (s, 2H) 2.95-3.09 (m, 1H) 3.10 (s, 3H) 3.94 (s, 3H) 6.68 (d, J=3.12 Hz, 1H) 7.22 (dd, J=5.95, 1.17 Hz, 2H) 7.33-7.51 (m, 1H).

Example 2

(2R)-4-[5-(2-Fluoro-3-methoxyphenyl)isoxazol-3-yl]-N-hydroxy-2-methyl-2-(methylsulfonyl)butanamide

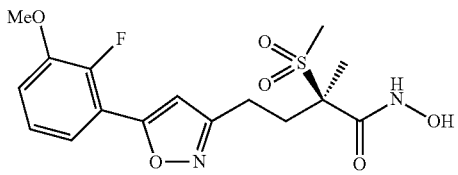 [SMILES: COc1cccc(-c2cc(CC[C@](C)(C(=O)NO)S(C)(=O)=O)no2)c1F]

Step A)

Ethyl(2R)-4-[5-(2-fluoro-3-methoxyphenyl)isoxazol-3-yl]-2-methyl-2-(methylsulfonyl)butanoate Sodium hypochlorite (6% aqueous solution, 6.0 mL, 4.8 mmol, 2.0 equiv) was added dropwise to a cooled (0-5° C.) and vigorously stirred solution of 1-ethynyl-2-fluoro-3-methoxybenzene (0.36 g, 2.4 mmol, 1.0 equiv) and ethyl(2R)-5-(hydroxyimino)-2-methyl-2-(methylsulfonyl)pentanoate (0.60 g, 2.4 mmol, 1.0 equiv) in dichloromethane (20 mL). The biphasic mixture was allowed to vigorously stir overnight (15 h) at room temperature. Water (50 mL) was added, and the mixture was extracted with dichloromethane (2×75 mL). The combined organic phases were dried over anhydrous magnesium sulfate, filtered and concentrated under reduced pressure. The crude material was purified by flash chromatography (25 g silica gel column, 0-20% gradient ethyl acetate in hexanes) to provide a light tan oil (0.50 g, 52%). MS (LCMS) m/z 400.3 (M+1). $^1$H NMR (400 MHz, METHONAL-d$_4$) δ1.26 (t, J=7.17 Hz, 3H) 1.71 (s, 2H) 2.24-2.42 (m, 2H) 3.09-3.20 (m, 5H) 3.95 (s, 3H) 4.12 (d, J=7.12 Hz, 2H) 6.74-6.85 (m, 1H) 7.18-7.34 (m, 2H) 7.41-7.54 (m, 1H).

Step B)

(2R)-4-[5-(2-Fluoro-3-methoxyphenyl)isoxazol-3-yl]-2-methyl-2-(methylsulfonyl)butanoic acid The title compound (0.46 g, 95%) was prepared from ethyl (2R)-4-[5-(2-fluoro-3-methoxyphenyl)isoxazol-3-yl]-2-methyl-2-(methylsulfonyl)butanoate (0.50 g, 1.25 mmol) by following the procedure described for the synthesis of (2R)-4-[3-(2-fluoro-3-methoxyphenyl)isoxazol-5-yl]-2-methyl-2-(methylsulfonyl)butanoic acid (Example 1, Step B). MS (GCMS) m/z 372.1 (M+1). $^1$H NMR (400 MHz, METHONAL-d$_4$) δ1.69 (s, 3H) 2.45-2.56 (m, 2H) 3.14 (d, J=9.95 Hz, 5H) 3.93 (s, 3H) 6.70-6.82 (m, 1H) 7.19-7.30 (m, 2H) 7.37-7.52 (m, 1H).

Step C)

(2R)-4-[5-(2-Fluoro-3-methoxyphenyl)isoxazol-3-yl]-N-hydroxy-2-methyl-2-(methylsulfonyl)butanamide N,N-Dimethy-4-aminopyridine (0.04 g, 0.3 mmol, 0.2 equiv), N-ethyl-N-isopropylpropan-2-amine (0.97 mL, 5.8 mmol, 4.5 equiv), T3P® (50% w/w solution in ethyl acetate, 3.0 mL, 4.96 mmol, 4.0 equiv), and (2R)-4-[5-(2-fluoro-3-methoxyphenyl)isoxazol-3-yl]-2-methyl-2-(methylsulfonyl)butanoic acid (0.46 g, 1.24 mmol, 1.0 equiv) were allowed to stir at room temperature for 30 min. A solution of O-(tetrahydro-2H-pyran-2-yl)hydroxylamine (0.16 g, 1.3 mmol, 1.2 equiv) in ethyl acetate (15 mL) was added, and the reaction was allowed to stir overnight (18 h) at room temperature. Water (40 mL) was added, and the mixture was extracted with ethyl acetate (2×50 mL). The combined organic phases were dried over anhydrous magnesium sulfate, filtered and concentrated under reduced pressure. The crude material was purified by flash chromatography (25 g silica gel column, 0-100% gradient ethyl acetate in hexanes) to provide (2R)-4-[5-(2-fluoro-3-methoxyphenyl)isoxazol-3-yl]-2-methyl-2-(methylsulfonyl)-N-(tetrahydro-2H-pyran-2-yloxy)butanamide (0.60 g, 10%). MS (LCMS) m/z 469.1 (M−1).

Hydrochloric acid (4.0 M in 1,4-dioxane, 0.13 mL, 0.51 mmol, 4 equiv) was added to a solution of (2R)-4-[5-(2-fluoro-3-methoxyphenyl)isoxazol-3-yl]-2-methyl-2-(methylsulfonyl)-N-(tetrahydro-2H-pyran-2-yloxy)butanamide (0.60 g, 0.13 mmol, 1.0 equiv) in 1,4-dioxane-dichloromethane-water (2:2:1, 2.5 mL), and the reaction was allowed to stir at room temperature for 2 h. The solvent was removed under reduced pressure, and the resulting crude material purified by preparative HPLC (Sepax 2-ethyl pyridine 250×21.2 mm 5 μm, heptane-ethanol solvent system as eluent) to provide (2R)-4-[5-(2-Fluoro-3-methoxyphenyl) isoxazol-3-yl]-N-hydroxy-2-methyl-2-(methylsulfonyl)butanamide butanamide (0.01 g, 20%). MS (LCMS) m/z 385.0 (M−1). $^1$H NMR (400 MHz, METHONAL-d$_4$) δ1.59-1.71 (m, 3H) 2.13-2.29 (m, 1H) 2.61-2.81 (m, 2H) 2.80-2.99 (m, 1H) 3.07 (s, 3H) 3.92 (s, 3H) 6.65-6.84 (m, 1H) 7.16-7.30 (m, 2H) 7.37-7.52 (m, 1H).

Examples 3-6

The compounds in Table 3 were prepared using similar procedures/conditions as described in Examples 1 and 2 and using the appropriate starting materials. The starting materials were prepared using synthetic methodology known to those skilled in the art.

TABLE 3

| Example | Compound Name | Mass Ion[1] | NMR |
|---|---|---|---|
| 3 | (2R)-4-[3-(2-fluoro-4-methoxyphenyl)isoxazol-5-yl]-N-hydroxy-2-methyl-2-(methylsulfonyl)butanamide | 387.1 | 1H NMR (400 MHz, METHANOL-d$_4$) δ 1.67 (s, 3H) 2.19-2.35 (m, 1H) 2.66-2.88 (m, 2H) 2.92-3.07 (m, 1H) 3.11 (s, 3H) 3.88 (s, 3H) 6.63 (d, J = 3.32 Hz, 1H) 6.75-6.97 (m, 2H) 7.82 (s, 1H) |
| 4 | (2R)-N-hydroxy-2-methyl-2-(methylsulfonyl)-4-(3-phenylisoxazol-5-yl)butanamide | 339.0 | 1H NMR (400 MHz, METHANOL-d$_4$) δ 1.68 (s, 3H) 2.19-2.39 (m, 1H) 2.72-2.92 (m, 2H) 2.93-3.08 (m, 1H) 3.12 (s, 3H) 6.72 (s, 1H) 7.39-7.56 (m, 3H) 7.76-7.92 (m, 2H) |
| 5 | (2R)-4-[5-(2-fluoro-4-methoxyphenyl)isoxazol-3-yl]-N-hydroxy-2-methyl-2-(methylsulfonyl)butanamide | 387.0 | $^1$H NMR (400 MHz ,METHANOL-d$_4$) δ 7.83 (d, J = 8.7 Hz, 2H), 7.11-6.82 (m, 2H), 6.65 (d, J = 3.6 Hz, 1H), 3.89 (s, 3H), 3.10 (s, 3H), 2.95-2.78 (m, 1H), 2.80-2.61 (m, 2H), 2.33-2.07 (m, 1H), 1.68 (s, 3H) |
| 6 | (2R)-N-hydroxy-2-methyl-2-(methylsulfonyl)-4-(5-phenylisoxazol-3-yl)butanamide | 339.1 | $^1$H NMR (400 MHz, DMSO-d$_6$) δ 1.55 (s, 3H) 1.99 (s, 1H) 2.52-2.70 (m, 2H) 2.71-2.90 (m, 1H) 3.08 (s, 3H) 7.03 (s, 1H) 7.53 (d, J = 7.22 Hz, 3H) 7.76-7.95 (m, 2H) 9.24 (d, J = 1.76 Hz, 1H) 10.74-11.11 (m, 1H) |

Example 7

4-[3-(5-ethyl-2-thieny)isoxazol-5-yl]-N-hydroxy-2-methyl-2-(methylsulfonyl)butanamide

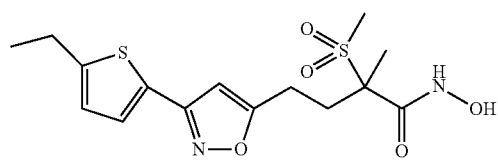 [SMILES: CCc1ccc(-c2cc(CCC(C)(C(=O)NO)S(C)(=O)=O)on2)s1]

Sodium hypochlorite (6% aqueous solution, 0.25 mL, 0.2 mmol, 1.3 equiv) was added dropwise to a vigorously stirred solution of 5-ethylthiophene-2-carbaldehyde oxime (23 mg, 0.15 mmol, 1.0 equiv) and ethyl 2-methyl-2-(methylsulfonyl) hex-5-ynoate (35 mg, 0.15 mmol, 1.0 equiv) in dichloromethane (1.0 mL). The reaction was allowed to stir at 30° C. for 16 h. Water (1.0 mL) was added to the reaction, the phases were separated, and the aqueous phase was extracted with dichloromethane (1.0 mL). The combined organic phases were concentrated under reduced pressure (SpeedVac).

The crude material was dissolved in tetrahydrofuran (0.7 mL). Lithium hydroxide (1.0 M aqueous solution, 0.7 mL) was added, and the reaction was shaken at 30° C. for 16 h. The solution was concentrated under reduced pressure (SpeedVac) to remove the tetrahydrofuran, and the resulting aqueous portion was acidified to pH=4-5 with citric acid (4.0 M aqueous solution, 0.1 mL). The mixture was extracted with ethyl acetate (2×1.0 mL). The combined organic phases were dried over anhydrous magnesium sulfate, filtered and concentrated under reduced pressure (SpeedVac).

The crude material was dissolved in dichloromethane (1.0 mL). (Aminooxy) (tert-butyl)dimethylsilane (14 mg, 0.1 mmol), N-ethyl-N-isopropylpropan-2-amine (35 uL, 0.2 mmol), and [bis(dimethylamino)methylene](3H-[1,2,3]triazolo[4,5-b]pyridin-3-yl)oxonium hexafluorophosphate (38 mg, 0.1 mmol) were added sequentially, and the reaction was shaken at 30° C. for 16 h. Hydrochloric acid (4.0 M solution in 1,4-dioxane, 40 uL) was added, and the reaction was shaken at 30° C. for 30 min. The solvent was removed under pressure (SpeedVac), and the crude material was purified by reverse phases preparative HPLC to provide the title compound. MS (LCMS) m/z 373.0 (M+1).

Example 8

4-[5-(2-Fluorophenyl)isoxazol-3-yl]-N-hydroxy-2-methyl-2-(methylsulfonyl)butanamide

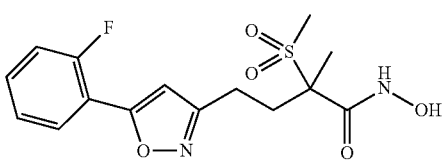 [SMILES: CC(CCc1cc(-c2ccccc2F)on1)(C(=O)NO)S(C)(=O)=O]

A solution of N-chlorosuccinimide (29 mg, 0.22 mmol, 1.8 equiv) and ethyl 5-(hydroxyimino)-2-methyl-2-(methylsulfonyl)pentanoate (51 mg, 0.2 mmol, 1.6 equiv) in N,N-dimethylformamide (0.5 mL) was shaken at 60° C. After 4 h, the reaction mixture was cooled to 0-5° C. A solution of 1-ethynyl-2-fluorobenzene (15 mg, 0.13 mmol, 1.0 equiv) in N,N- dimethylformamide (0.25 mL) and triethylamine (36 uL, 0.25 mmol, 2.0 equiv) were added, and the mixture was shaken at 0° C. for 1 h. The reaction was heated to 60° C., shaken for 16 h, and then concentrated under reduced pressure (SpeedVac).

The crude material was dissolved in methanol (1.0 mL), treated with lithium hydroxide (1.0 M aqueous solution, 0.5 mL), and shaken at 30° C. for 16 h. The reaction was concentrated under reduced pressure (SpeedVac), and the resulting residue was dissolved in acetonitrile (1.0 mL) and water (0.5 mL). After acidification to pH=6 with 2.0 M hydrochloric acid (approx. 0.1 mL), the crude material was purified by preparative HPLC.

The purified carboxylic acid intermediate was dissolved in a solution of (aminooxy)(tert-butyl)dimethylsilane (0.4 M in N,N-dimethylformamide, 0.25 mL, 0.1 mmol). Triethylamine (21 uL, 0.15 mmol) and a solution of [bis(dimethylamino)methylene](3H-[1,2,3]triazolo[4,5-b]pyridin-3-yl) oxonium hexafluorophosphate (0.4 M in N,N-dimethylformamide, 0.25 mL, 0.1 mmol) were added sequentially, and the reaction as shaken at 30° C. for 16 h. The solvent was removed under pressure (SpeedVac), and the crude material was purified by reverse phases preparative HPLC to provide the title compound. MS (LCMS) m/z 357.1 (M+1).

Biological Examples

In order to assess the compounds biological activity selected in vitro assays were conducted on selected compounds. One of the assays measured the compounds ability to disrupt the synthesis of lipopolysaccharide, LPS, which is a component of the outer membrane of Gram-negative bacteria. Disruption of this synthesis is lethal to the bacteria. The assay determined the compound's ability to inhibit LpxC, which is the first enzyme in the biosynthetic pathway for LPS (measured as $IC_{50}$). Additionally, MICs (minimal inhibitory concentrations) were determined for several bacteria. The specific protocols are described below:

A) $IC_{50}$ Assay LpxC Enzyme from *P. aeruginosa* Labeled as PA LpxC Enzyme $IC_{50}$):

$IC_{50}$ determination in the LpxC enzyme assay was carried out in a similar manner to that described by Malikzay et al. in the 2006 Poster, Screening LpxC (UDP-3-O—(R-3-hydroxymyristoyl)-GlcNAc deacetylase) using BioTrove RapidFire HTS Mass Spectrometry (aNew Lead Discovery and bInflammation and Infectious Disease, cStructural Chemistry, Schering-Plough Research Institute, Kenilworth, N.J. 07033, (BioTrove, Inc. 12 Gill St., Suite 4000, Woburn, Mass. 01801). Briefly, *Pseudomonas aeruginosa* LpxC enzyme (0.1 nM) purified from *E. coli*-overexpressing bacteria was incubated at 25° C. in a final volume of 50 ul containing 0.5 uM UDP-3-O—(R-3-hydroxydecanoyl)-N-acetylglucosamine, 1 mg/mL BSA, and 50 mM sodium phosphate buffer, pH 8.0 in the presence and absence of inhibitor compound. At the end of 1 hour, 5 ul of 1 N HCl was added to stop the enzyme reaction, the plates were centrifuged, and then processed with the BioTrove Rapidfire HTMS Mass Spectrometry System. A no-enzyme control was used in calculating the $IC_{50}$ values from the percent conversion values.

B) MIC Determinations:

The in vitro antibacterial activity of compounds described in the Examples was evaluated by minimum inhibitory concentration (MIC) testing according to Clinical and Laboratory Standards Institute (CLSI). See: Clinical and Laboratory Standards Institute. Methods for Dilution Antimicrobial Susceptibility Tests for Bacteria that Grow Aerobically; Approved Standard-Eighth Edition. CLSI document M7-A8 [ISBN 1-56238-689-1]. Clinical and Laboratory Standards Institute, 940 West Valley Road, Suite 1400, Wayne, Pa. 19087-1898 USA, 2006; also Clinical and Laboratory Standards Institute. Performance Standards for Antimicrobial Susceptibility Testing; Twentieth Informational Supplement. CLSI document M100-S20 [ISBN1-56238-716-2]. Clinical and Laboratory Standards Institute.

The MIC determination is a standard laboratory method for evaluating the antibacterial activity of a compound. The MIC represents the lowest drug concentration that inhibits visible growth of bacteria following overnight incubation. In order to determine the MIC value, a range of drug concentrations (e.g., 0.06 µg/mL to 64 µg/mL) are incubated with a defined strain of bacteria. Typically, the drug concentration range is broken down into 2-fold increments (e.g., 0.06 µg/mL, 0.12 µg/mL. 0.25 µg/mL, 0.50 µg/mL, 1.0 µg/mL, etc.) and the various drug concentrations are all individually incubated overnight with approximately the same number of bacteria. The MIC is then determined by visually inspecting the drug effect at each concentration, and identifying the lowest drug concentration that has inhibited bacterial growth as compared to the drug free control. Typically, bacteria continue to grow at drug concentrations lower than the MIC and don't grow at concentrations at and above the MIC.

The MIC values described in Tables 4 and 5 below were derived from assays wherein each test compound was evaluated in duplicate. In cases where the duplicate values varied by 0-2-fold, the lower of the two values was reported below. Generally speaking, if the duplicate values varied by more than 2-fold, the assay was considered non-valid and was repeated until the variation between duplicate runs was 2-fold. In line with the CLSI guidelines referred to above, both control organisms and reference compounds were utilized in each MIC assay to provide proper quality control. MIC values generated with these control organisms and reference compounds were required to fall within a defined range for the assay to be considered valid and be included herein. Those skilled in the art will recognize that MIC values can and do vary from experiment to experiment. Generally speaking, it should be recognized that MIC values often vary +/−2-fold from experiment to experiment. While a single MIC is reported for each compound and each microorganism, the reader should not conclude that each compound was only tested once. Several of the compounds were subjected to multiple tests. The data reported in Tables 4 and 5 is reflective of the compound's relative activity and different MICs may have been generated on these occasions in line with the guidelines described above.

The following bacterial strains were used in these MIC determinations:

1) *Pseudomonas aeruginosa* UC12120 (mouse virulent) labeled as PA-UC12120 in Tables 4 and 5;

2) *Escherichia coli* EC-1: VOGEL, mouse virulent labeled as EC-1 in Tables 4 and 5;

3) *Acinetobacter baumannii/haemolyticus*: Multidrug-resistant clinical isolate labeled as AB-3167 in Tables 4 and 5;

Tables 4 and 5, below, show the results that were obtained with the final products described in Examples 1-50. If a particular table entry is blank, then the data was not available at the current time.

Column 1 corresponds to the Example number, column 2 provides the compound name, column 3 provides the results from the LpxC enzyme assay described above, and columns 4-6 provide the MIC data as described above.

TABLE 4

| Example | Compound Name | PA:IC50 (μM) | PA-UC12120 (μg/mL) | EC-1 (μg/mL) | AB-3167 (μg/mL) |
|---|---|---|---|---|---|
| 1 | (2R)-4-[3-(2-fluoro-3-methoxyphenyl)isoxazol-5-yl]-N-hydroxy-2-methyl-2-(methylsulfonyl)butanamide | 0.00532 | 2 | 4 | >64 |
| 2 | (2R)-4-[5-(2-fluoro-3-methoxyphenyl)isoxazol-3-yl]-N-hydroxy-2-methyl-2-(methylsulfonyl)butanamide | | 16 | 16 | 32 |
| 3 | (2R)-4-[3-(2-fluoro-4-methoxyphenyl)isoxazol-5-yl]-N-hydroxy-2-methyl-2-(methylsulfonyl)butanamide | 0.0044 | 0.5 | 4 | >64 |
| 4 | (2R)-N-hydroxy-2-methyl-2-(methylsulfonyl)-4-(3-phenylisoxazol-5-yl)butanamide | 0.00578 | 0.25 | 4 | >64 |
| 5 | (2R)-4-[5-(2-fluoro-4-methoxyphenyl)isoxazol-3-yl]-N-hydroxy-2-methyl-2-(methylsulfonyl)butanamide | | 0.25 | 4 | >64 |
| 6 | (2R)-N-hydroxy-2-methyl-2-(methylsulfonyl)-4-(5-phenylisoxazol-3-yl)butanamide | 0.00051 | 0.25 | 8 | >64 |

Examples 7-50

Examples 7-50 in Table 5 were prepared using similar procedures/conditions as outlined in Examples 7 and 8. As described in the Synthesis section (Schemes 1 and 2), products are derived from a 1,3-dipolar cycloadditions of nitrile oxides (generate in situ) with alkynes, In Table 5 (below), column 2 provides the compound name, columns 3-6 provide in vitro biological data generated in the same manner as in Table 4, column 7 and 8 provide the mass observed and retention times generated with LCMS using Method A, B or C (column 9), as described below.

Method A
  Column: Acquity UPLC BEH C18 2.1×30 mm 1.7 μm
  Flow rate: 1.3 mL/min
  Solvent A: 0.05% TFA in water
  Solvent B: 0.05% TFA in acetonitrile
  Gradient: 0.00 min—95% A, 5% B
    1.10 min—5% A, 95% B Method B
  Column: Xbridge C18 2.1×50 mm 5 μm
  Flow rate: 0.8 mL/min
  Solvent A: 0.0375% TFA in water
  Solvent B: 0.01875% TFA in acetonitrile
  Gradient: 0.00 min—99% A, 1% B
    0.60 min—95% A, 5% B
    4.00 min—0% A, 100% B
    4.30 min—99% A, 1% B
    4.70 min—99% A, 1% B Method C
  Column: Xbridge C18 2.1×50 mm 5 μm
  Flow rate: 0.8 mL/min
  Solvent A: 0.05% NH$_4$OH in water
  Solvent B: acetonitrile
  Gradient: 0.00 min—95% A, 5% B
    0.50 min—95% A, 5% B
    3.40 min—0% A, 100% B
    4.20 min—0% A, 100% B
    4.21 min—95% A, 5% B
    4.70 min—95% A, 5% B

TABLE 5

| Ex. No. | Compound Name | PA:IC50 (μM) | PA-UC12120 (μg/mL) | EC-1 (μg/mL) | AB-3167 (μg/mL) | Mass | Retention Time | Method |
|---|---|---|---|---|---|---|---|---|
| 7 | 4-[3-(5-ethyl-2-thienyl)isoxazol-5-yl]-N-hydroxy-2-methyl-2-(methylsulfonyl)butanamide | 0.0011 | 0.5 | 4 | 64 | 373.0 | 0.63 | A |
| 8 | 4-[5-(2-fluorophenyl)isoxazol-3-yl]-N-hydroxy-2-methyl-2-(methylsulfonyl)butanamide | 0.0083 | 1 | 16 | >64.0 | 357.1 | 0.57 | A |
| 9 | 4-{5-[(benzyloxy)methyl]isoxazol-3-yl}-N-hydroxy-2-methyl-2-(methylsulfonyl)butanamide | 0.0251 | 8 | >64.0 | >64.0 | 383.1 | 0.6 | A |
| 10 | 4-[5-(2,6-dichlorophenyl)isoxazol-3-yl]-N-hydroxy-2-methyl-2-(methylsulfonyl)butanamide | 0.0105 | 64 | 8 | >64.0 | 407.0 | 0.61 | A |
| 11 | N-({3-[4-(hydroxyamino)-3-methyl-3-(methylsulfonyl)-4-oxobutyl]isoxazol-5-yl}methyl)-4-methoxybenzamide | | >64.0 | >64.0 | >64.0 | 426.0 | 2.293 | B |
| 12 | N-hydroxy-4-{5-[(2-methoxyphenoxy)methyl]isoxazol-3-yl}-2-methyl-2-(methylsulfonyl)butanamide | 0.0374 | >64.0 | >64.0 | >64.0 | 399.0 | 2.577 | B |
| 13 | N-hydroxy-2-methyl-4-[5-(3-methylphenyl)isoxazol-3-yl]-2-(methylsulfonyl)butanamide | | 1 | 32 | 64 | 353.0 | 2.795 | B |

TABLE 5-continued

| Ex. No. | Compound Name | PA:IC50 (µM) | PA-UC12120 (µg/mL) | EC-1 (µg/mL) | AB-3167 (µg/mL) | Mass | Retention Time | Method |
|---|---|---|---|---|---|---|---|---|
| 14 | S-butyl ({3-[4-(hydroxyamino)-3-methyl-3-(methylsulfonyl)-4-oxobutyl]isoxazol-5-yl}methyl)methylthiocarbamate | >0.1 | >64.0 | >64.0 | >64.0 | 422.1 | 0.76 | A |
| 15 | N-hydroxy-4-[5-(9-hydroxynonyl)isoxazol-3-yl]-2-methyl-2-(methylsulfonyl)butanamide | | 4 | 16 | >64.0 | 405.0 | 2.137 | C |
| 16 | N-hydroxy-4-[5-(2-methoxyphenyl)isoxazol-3-yl]-2-methyl-2-(methylsulfonyl)butanamide | 0.0405 | 16 | >64.0 | >64.0 | 369.1 | 0.58 | A |
| 17 | N-hydroxy-4-{5-[(1-hydroxycyclohexyl)methyl]isoxazol-3-yl}-2-methyl-2-(methylsulfonyl)butanamide | >0.1 | >64.0 | >64.0 | >64.0 | 375.1 | 0.49 | A |
| 18 | 4-(5-{[cyclopropyl(2-phenoxyethyl)amino]methyl}isoxazol-3-yl)-N-hydroxy-2-methyl-2-(methylsulfonyl)butanamide | | >64.0 | >64.0 | >64.0 | 452.0 | 2.247 | C |
| 19 | N-hydroxy-4-(5-{[(2-methoxyphenyl)thio]methyl}isoxazol-3-yl)-2-methyl-2-(methylsulfonyl)butanamide | | 64 | >64.0 | >64.0 | 415.0 | 2.711 | B |
| 20 | 4-[5-(3,4-dichlorophenyl)isoxazol-3-yl]-N-hydroxy-2-methyl-2-(methylsulfonyl)butanamide | | 1 | 4 | 16 | 407.0 | 2.193 | C |
| 21 | 4-[5-(3-fluorophenyl)isoxazol-3-yl]-N-hydroxy-2-methyl-2-(methylsulfonyl)butanamide | 0.0068 | 4 | 32 | >64.0 | 357.1 | 0.58 | A |
| 22 | 4-{5-[4-(difluoromethoxy)-3-methylphenyl]isoxazol-3-yl}-N-hydroxy-2-methyl-2-(methylsulfonyl)butanamide | 0.0015 | 1 | 8 | >64.0 | 419.1 | 0.64 | A |
| 23 | ethyl ({3-[4-(hydroxyamino)-3-methyl-3-(methylsulfonyl)-4-oxobutyl]isoxazol-5-yl}methyl)isopropylcarbamate | >0.1 | >64.0 | >64.0 | >64.0 | 406.1 | 0.53 | A |
| 24 | 4-[5-(2,6-dimethoxyphenyl)isoxazol-3-yl]-N-hydroxy-2-methyl-2-(methylsulfonyl)butanamide | >0.1 | >64.0 | >64.0 | >64.0 | 399.1 | 0.55 | A |
| 25 | {3-[4-(hydroxyamino)-3-methyl-3-(methylsulfonyl)-4-oxobutyl]isoxazol-5-yl}methyl butylcarbamate | >0.1 | >64.0 | >64.0 | >64.0 | 392.1 | 0.52 | A |
| 26 | 4-{5-[(1,3-benzodioxol-5-yloxy)methyl]isoxazol-3-yl}-N-hydroxy-2-methyl-2-(methylsulfonyl)butanamide | | 4 | 16 | >64.0 | 413.0 | 2.612 | B |
| 27 | 4-[5-({[(4-fluorophenyl)sulfonyl]amino}methyl)isoxazol-3-yl]-N-hydroxy-2-methyl-2-(methylsulfonyl)butanamide | >0.1 | >64.0 | >64.0 | >64.0 | 450.1 | 0.51 | A |
| 28 | 4-[5-(2,4-difluorophenyl)isoxazol-3-yl]-N-hydroxy-2-methyl-2-(methylsulfonyl)butanamide | 0.0028 | | | | 375.1 | 0.59 | A |
| 29 | N-hydroxy-4-[5-(3-methoxyphenyl)isoxazol-3-yl]-2-methyl-2-(methylsulfonyl)butanamide | | 8 | 64 | >64.0 | 369.0 | 2.663 | B |
| 30 | 4-[5-(2,3-dichlorophenyl)isoxazol-3-yl]-N-hydroxy-2-methyl-2-(methylsulfonyl)butanamide | 0.0027 | 1 | 4 | >64.0 | 407.0 | 0.65 | A |
| 31 | 4-[3-(1-ethoxy-1-methylethyl)isoxazol-5-yl]-N-hydroxy-2-methyl-2-(methylsulfonyl)butanamide | >0.1 | >64.0 | >64.0 | >64.0 | 349.1 | 0.48 | A |
| 32 | 4-[3-(2,6-dimethoxyphenyl)isoxazol-5-yl]-N-hydroxy-2-methyl-2-(methylsulfonyl)butanamide | 0.0887 | >64.0 | >64.0 | >64.0 | 399.1 | 0.52 | A |
| 33 | 4-[3-(1,3-benzodioxol-5-yl)isoxazol-5-yl]-N-hydroxy-2-methyl-2-(methylsulfonyl)butanamide | 0.0051 | 2 | 16 | >64.0 | 383.0 | 0.54 | A |
| 34 | 4-[3-(3-fluorophenyl)isoxazol-5-yl]-N-hydroxy-2-methyl-2-(methylsulfonyl)butanamide | 0.0093 | 2 | 32 | >64.0 | 357.0 | 0.58 | A |
| 35 | N-hydroxy-2-methyl-2-(methylsulfonyl)-4-(3-quinolin-2-ylisoxazol-5-yl)butanamide | 0.0221 | 8 | 32 | >64.0 | 390.1 | 0.57 | A |
| 36 | N-hydroxy-2-methyl-2-(methylsulfonyl)-4-[3-(2,3,4-trifluorophenyl)isoxazol-5-yl]butanamide | 0.0039 | 1 | 16 | >64.0 | 393.0 | 0.61 | A |
| 37 | 4-[3-(3-fluoropyridin-4-yl)isoxazol-5-yl]-N-hydroxy-2-methyl-2-(methylsulfonyl)butanamide | 0.0524 | 16 | >64.0 | >64.0 | 358.0 | 0.41 | A |
| 38 | N-hydroxy-2-methyl-4-[3-(4-methylphenyl)isoxazol-5-yl]-2-(methylsulfonyl)butanamide | 0.0029 | 1 | 8 | >64.0 | 353.1 | 0.6 | A |
| 39 | N-hydroxy-2-methyl-2-(methylsulfonyl)-4-[3-(2-phenylethyl)isoxazol-5-yl]butanamide | 0.0098 | 4 | 32 | >64.0 | 367.1 | 0.6 | A |
| 40 | N-hydroxy-2-methyl-2-(methylsulfonyl)-4-(3-quinolin-3-ylisoxazol-5-yl)butanamide | 0.0252 | | | | 390.1 | 0.44 | A |
| 41 | 4-[3-(3,4-difluorophenyl)isoxazol-5-yl]-N-hydroxy-2-methyl-2-(methylsulfonyl)butanamide | 0.0068 | 2 | 16 | >64.0 | 375.0 | 0.6 | A |
| 42 | 4-[3-(3,4-dimethoxyphenyl)isoxazol-5-yl]-N-hydroxy-2-methyl-2-(methylsulfonyl)butanamide | 0.0386 | 64 | >64.0 | >64.0 | 399.1 | 0.5 | A |
| 43 | 4-[3-(3-fluoropyridin-2-yl)isoxazol-5-yl]-N-hydroxy-2-methyl-2-(methylsulfonyl)butanamide | >0.1 | 32 | 64 | >64.0 | 358.0 | 0.42 | A |
| 44 | 4-[3-(4-fluorophenyl)isoxazol-5-yl]-N-hydroxy-2-methyl-2-(methylsulfonyl)butanamide | 0.0038 | 1 | 16 | >64.0 | 357.0 | 0.57 | A |
| 45 | N-cyclohexyl-5-[4-(hydroxyamino)-3-methyl-3-(methylsulfonyl)-4-oxobutyl]isoxazole-3-carboxamide | | >64.0 | >64.0 | >64.0 | 388.1 | 0.55 | A |

TABLE 5-continued

| Ex. No. | Compound Name | PA:IC50 (µM) | PA-UC12120 (µg/mL) | EC-1 (µg/mL) | AB-3167 (µg/mL) | Mass | Retention Time | Method |
|---|---|---|---|---|---|---|---|---|
| 46 | N-hydroxy-2-methyl-2-(methylsulfonyl)-4-(3-quinolin-4-ylisoxazol-5-yl)butanamide | 0.0054 | | | | 390.1 | 0.4 | A |
| 47 | N-hydroxy-4-[3-(4-methoxyphenyl)isoxazol-5-yl]-2-methyl-2-(methylsulfonyl)butanamide | 0.0041 | 1 | 16 | >64.0 | 369.1 | 0.55 | A |
| 48 | 4-[3-(3-fluoro-4-morpholin-4-ylphenyl)isoxazol-5-yl]-N-hydroxy-2-methyl-2-(methylsulfonyl)butanamide | 0.0242 | 32 | 32 | >64.0 | 442.1 | 0.56 | A |
| 49 | N-hydroxy-4-[3-(2-methoxyphenyl)isoxazol-5-yl]-2-methyl-2-(methylsulfonyl)butanamide | 0.0424 | 32 | >64.0 | >64.0 | 369.1 | 0.55 | A |
| 50 | 4-[3-(2,4-difluorophenyl)isoxazol-5-yl]-N-hydroxy-2-methyl-2-(methylsulfonyl)butanamide | | 1 | 16 | >64.0 | 375.0 | 0.58 | A |

We claim:

1. A compound of Formula I or Formula II

Formula I

Formula II or a pharmaceutically acceptable salt thereof, wherein
$R^1$ is ($C_1$-$C_3$)alkyl;
$R^2$ is hydrogen or ($C_1$-$C_3$)alkyl;
$R^3$ is hydrogen, ($C_1$-$C_3$)alkoxy, ($C_1$-$C_3$)alkyl, cyano, ($C_1$-$C_3$)haloalkoxy, ($C_1$-$C_3$)haloalkyl, halogen, or hydoxy;
L is a bond, —$(CH_2)_n$—, —$(CH_2)_nO(CH_2)_p$—, —$(CH_2)_nS(CH_2)_p$—, —$(CH_2)_nNR^4(CH_2)_p$—, —$(CH_2)_nSO_2NR^4(CH_2)_p$—, —$(CH_2)_nNR^4SO_2(CH_2)_p$—, —$(CH_2)_nCONR^4(CH_2)_p$—, or —$(CH_2)_nNR^4CO(CH_2)_p$—;
$R^4$ and $R^5$ are independently hydrogen, ($C_1$-$C_6$)alkyl, ($C_1$-$C_6$)alkylcarbonyl, ($C_3$-$C_8$)cycloalkyl, ($C_3$-$C_8$)cycloalkyl($C_1$-$C_6$)alkyl, or formyl;
n is 0, 1, 2, 3, or 4;
p is 0, 1, 2, 3, or 4;
$R^6$ is ($C_1$-$C_6$)alkoxy($C_1$-$C_6$)alkyl, ($C_1$-$C_6$)alkoxycarbonyl, ($C_1$-$C_6$)alkylcarbonyl, ($C_1$-$C_6$)alkyl-$NR^4$—($C_1$-$C_6$)alkyl, ($C_1$-$C_6$)alkylthio($C_1$-$C_6$)alkyl, ($C_1$-$C_6$)alkylthiocarbonyl, ($C_6$-$C_{12}$)aryl, ($C_6$-$C_{12}$)aryloxy, ($C_6$-$C_{12}$)arylthio, ($C_6$-$C_{12}$)aryl-$NR^4$—, ($C_3$-$C_8$)cycloalkyl, ($C_3$-$C_8$)cycloalkyloxy, ($C_3$-$C_8$)cycloalkylthio, ($C_3$-$C_8$)cycloalkyl-$NR^4$—, ($C_5$-$C_{12}$)heteroaryl, ($C_5$-$C_{12}$)heteroaryloxy, ($C_5$-$C_{12}$)heteroarylthio, ($C_5$-$C_{12}$)heteroaryl-$NR^4$—, ($C_3$-$C_{13}$)heterocycle, ($C_3$-$C_{13}$)heterocycleoxy, ($C_3$-$C_{13}$)heterocyclethio, ($C_3$-$C_{13}$)heterocycle-$NR^4$—, hydroxy($C_1$-$C_{10}$)alkyl, mercapto($C_1$-$C_6$)alkyl, ($NR^4R^5$)alkyl, or ($NR^4R^5$)carbonyl; and
$R^7$ is absent, ($C_6$-$C_{12}$)aryl, ($C_6$-$C_{12}$)aryl($C_1$-$C_6$)alkyl, ($C_3$-$C_8$)cycloalkyl, ($C_3$-$C_8$)cycloalkyl($C_1$-$C_6$)alkyl, ($C_5$-$C_{12}$)heteroaryl, ($C_5$-$C_{12}$)heteroaryl($C_1$-$C_6$)alkyl, ($C_3$-$C_{13}$)heterocycle, or ($C_3$-$C_{13}$)heterocycle($C_1$-$C_6$)alkyl.

2. The compound according to claim 1 wherein
$R^1$ is ($C_1$-$C_3$)alkyl;
$R^2$ is ($C_1$-$C_3$)alkyl;
$R^3$ is hydrogen;
L is a bond, —$(CH_2)_n$—, —$(CH_2)_nO(CH_2)_p$—, —$(CH_2)_nS(CH_2)_p$—, —$(CH_2)_nNR^4(CH_2)_p$—, —$(CH_2)_nSO_2NR^4(CH_2)_p$—, —$(CH_2)_nCONR^4(CH_2)_p$—, or —$(CH_2)_nNR^4CO(CH_2)_p$—;
$R^4$ and $R^5$ are independently hydrogen, ($C_1$-$C_6$)alkyl, or ($C_3$-$C_8$)cycloalkyl;
n is 0, 1, or 2;
p is 0, 1, or 2;
$R^6$ is ($C_1$-$C_6$)alkoxy($C_1$-$C_6$)alkyl, ($C_1$-$C_6$)alkoxycarbonyl, ($C_1$-$C_6$)alkylthiocarbonyl, ($C_6$-$C_{12}$)aryl, ($C_6$-$C_{12}$)aryloxy, ($C_3$-$C_8$)cycloalkyl, ($C_5$-$C_{12}$)heteroaryl, hydroxy($C_1$-$C_{10}$)alkyl, or ($NR^4R^5$)carbonyl; and
$R^7$ is absent or ($C_3$-$C_{13}$)heterocycle.

3. The compound according to claim 1 wherein
$R^1$ is methyl;
$R^2$ is methyl;
$R^3$ is hydrogen;
L is a bond, —$(CH_2)_n$—, —$(CH_2)_nO(CH_2)_p$—, —$(CH_2)_nS(CH_2)_p$—, —$(CH_2)_nNR^4(CH_2)_p$—, —$(CH_2)_nSO_2NR^4(CH_2)_p$—, —$(CH_2)_nCONR^4(CH_2)_p$—, or —$(CH_2)_nNR^4CO(CH_2)_p$—;
$R^4$ is hydrogen, ($C_1$-$C_6$)alkyl, or ($C_3$-$C_8$)cycloalkyl;
n is 0, 1, or 2;
p is 0, 1, or 2;
$R^6$ is ($C_6$-$C_{12}$)aryl or ($C_6$-$C_{12}$)aryloxy, wherein the ($C_6$-$C_{12}$)aryl group for each is phenyl optionally substituted with 1, 2, or 3 substituents that are independently ($C_1$-$C_6$)alkoxy, ($C_1$-$C_6$)alkyl, halo($C_1$-$C_6$)alkoxy, halogen, or methylenedioxy; and
$R^7$ is absent or ($C_3$-$C_{13}$)heterocycle, wherein the ($C_3$-$C_{13}$)heterocycle is morpholinyl.

4. The compound according to claim 1 wherein
$R^1$ is methyl;
$R^2$ is methyl;
$R^3$ is hydrogen;
L is a bond, —$(CH_2)_2$—, —$O(CH_2)$—, —$(CH_2)O(CH_2)$—, —$S(CH_2)$—, —$(CH_2)_2NR^4(CH_2)$—, —$SO_2NR^4(CH_2)$—, or —$CONR^4(CH_2)$—;
$R^4$ is hydrogen, ($C_1$-$C_6$)alkyl, or ($C_3$-$C_8$)cycloalkyl;
$R^6$ is ($C_6$-$C_{12}$)aryl or ($C_6$-$C_{12}$)aryloxy, wherein the ($C_6$-$C_{12}$)aryl group for each is phenyl optionally substituted with 1, 2, or 3 substituents that are independently ($C_1$-$C_6$)alkoxy, ($C_1$-$C_6$)alkyl, halo($C_1$-$C_6$)alkoxy, halogen, or methylenedioxy; and
$R^7$ is absent or ($C_3$-$C_{13}$)heterocycle, wherein the ($C_3$-$C_{13}$)heterocycle is morpholinyl.

5. The compound according to claim 1 that is
(2R)-4-[3-(2-fluoro-3-methoxyphenyl)isoxazol-5-yl]-N-hydroxy-2-methyl-2-(methylsulfonyl)butanamide;
(2R)-4-[5-(2-fluoro-3-methoxyphenyl)isoxazol-3-yl]-N-hydroxy-2-methyl-2-(methylsulfonyl)butanamide;
(2R)-4-[3-(2-fluoro-4-methoxyphenyl)isoxazol-5-yl]-N-hydroxy-2-methyl-2-(methylsulfonyl)butanamide;
(2R)—N-hydroxy-2-methyl-2-(methylsulfonyl)-4-(3-phenylisoxazol-5-yl)butanamide;
(2R)-4-[5-(2-fluoro-4-methoxyphenyl)isoxazol-3-yl]-N-hydroxy-2-methyl-2-(methylsulfonyl)butanamide;
(2R)—N-hydroxy-2-methyl-2-(methylsulfonyl)-4-(5-phenylisoxazol-3-yl)butanamide;
4-[5-(2-fluorophenyl)isoxazol-3-yl]-N-hydroxy-2-methyl-2-(methylsulfonyl)butanamide;
4-{5-[(benzyl oxy)methyl]isoxazol-3-yl}-N-hydroxy-2-methyl-2-(methylsulfonyl)butanamide;
4-[5-(2,6-dichlorophenyl)isoxazol-3-yl]-N-hydroxy-2-methyl-2-(methylsulfonyl)butanamide;
N-({3-[4-(hydroxyamino)-3-methyl-3-(methylsulfonyl)-4-oxobutyl]isoxazol-5-yl}methyl)-4-methoxybenzamide;
N-hydroxy-4-{5-[(2-methoxyphenoxy)methyl]isoxazol-3-yl}-2-methyl-2-(methylsulfonyl)butanamide;
N-hydroxy-2-methyl-4-[5-(3-methylphenyl)isoxazol-3-yl]-2-(methylsulfonyl)butanamide;
N-hydroxy-4-[5-(2-methoxyphenyl)isoxazol-3-yl]-2-methyl-2-(methylsulfonyl)butanamide;
4-(5-{[cyclopropyl(2-phenoxyethyl)amino]methyl}isoxazol-3-yl)-N-hydroxy-2-methyl-2-(methylsulfonyl)butanamide;
N-hydroxy-4-(5-{[(2-methoxyphenyl)thio]methyl}isoxazol-3-yl)-2-methyl-2-(methylsulfonyl)butanamide;
4-[5-(3,4-dichlorophenyl)isoxazol-3-yl]-N-hydroxy-2-methyl-2-(methylsulfonyl)butanamide;
4-[5-(3-fluorophenyl)isoxazol-3-yl]-N-hydroxy-2-methyl-2-(methylsulfonyl)butanamide;
4-{5-[4-(difluoromethoxy)-3-methylphenyl]isoxazol-3-yl}-N-hydroxy-2-methyl-2-(methylsulfonyl)butanamide;
4-[5-(2,6-dimethoxyphenyl)isoxazol-3-yl]-N-hydroxy-2-methyl-2-(methylsulfonyl)butanamide;
4-{5-[(1,3-benzodioxol-5-yloxy)methyl]isoxazol-3-yl}-N-hydroxy-2-methyl-2-(methylsulfonyl)butanamide;
4-[5-({[(4-fluorophenyl)sulfonyl]amino}methyl)isoxazol-3-yl]-N-hydroxy-2-methyl-2-(methylsulfonyl)butanamide;
4-[5-(2,4-difluorophenyl)isoxazol-3-yl]-N-hydroxy-2-methyl-2-(methylsulfonyl)butanamide;
N-hydroxy-4-[5-(3-methoxyphenyl)isoxazol-3-yl]-2-methyl-2-(methylsulfonyl)butanamide;
4-[5-(2,3-dichlorophenyl)isoxazol-3-yl]-N-hydroxy-2-methyl-2-(methylsulfonyl)butanamide;
4-[3-(2,6-dimethoxyphenyl)isoxazol-5-yl]-N-hydroxy-2-methyl-2-(methylsulfonyl)butanamide;
4-[3-(1,3-benzodioxol-5-yl)isoxazol-5-yl]-N-hydroxy-2-methyl-2-(methylsulfonyl)butanamide;
4-[3-(3-fluorophenyl)isoxazol-5-yl]-N-hydroxy-2-methyl-2-(methylsulfonyl)butanamide;
N-hydroxy-2-methyl-2-(methylsulfonyl)-4-[3-(2,3,4-trifluorophenyl)isoxazol-5-yl]butanamide;
N-hydroxy-2-methyl-4-[3-(4-methylphenyl)isoxazol-5-yl]-2-(methylsulfonyl)butanamide;
N-hydroxy-2-methyl-2-(methylsulfonyl)-4-[3-(2-phenylethyl)isoxazol-5-yl]butanamide;
4-[3-(3,4-difluorophenyl)isoxazol-5-yl]-N-hydroxy-2-methyl-2-(methylsulfonyl)butanamide;
4-[3-(3,4-dimethoxyphenyl)isoxazol-5-yl]-N-hydroxy-2-methyl-2-(methylsulfonyl)butanamide;
4-[3-(4-fluorophenyl)isoxazol-5-yl]-N-hydroxy-2-methyl-2-(methylsulfonyl)butanamide;
N-hydroxy-4-[3-(4-methoxyphenyl)isoxazol-5-yl]-2-methyl-2-(methylsulfonyl)butanamide;
4-[3-(3-fluoro-4-morpholin-4-ylphenyl)isoxazol-5-yl]-N-hydroxy-2-methyl-2-(methylsulfonyl)butanamide;
N-hydroxy-4-[3-(2-methoxyphenyl)isoxazol-5-yl]-2-methyl-2-(methylsulfonyl)butanamide;
4-[3-(2,4-difluorophenyl)isoxazol-5-yl]-N-hydroxy-2-methyl-2-(methylsulfonyl)butanamide;
or a pharmaceutically acceptable salt thereof.

6. The compound according to claim 1 wherein
$R^1$ is methyl;
$R^2$ is methyl;
$R^3$ is hydrogen;
L is a bond, —$(CH_2)_n$—, —$(CH_2)_nO(CH_2)_p$—, —$(CH_2)_nS(CH_2)_p$—, —$(CH_2)_nNR^4(CH_2)_p$—, —$(CH_2)_nSO_2NR^4(CH_2)_p$—, —$(CH_2)_nCONR^4(CH_2)_p$—, or —$(CH_2)_nNR^4CO(CH_2)_p$—;
$R^4$ is hydrogen, $(C_1-C_6)$alkyl, or $(C_3-C_8)$cycloalkyl;
n is 0, 1, or 2;
p is 0, 1, or 2;
$R^6$ is $(C_5-C_{12})$heteroaryl, wherein the $(C_5-C_{12})$heteroaryl is pyridinyl, quinolinyl, or thienyl each optionally substituted with 1 substituent that is $(C_1-C_6)$alkyl or halogen; and
$R^7$ is absent.

7. The compound according to claim 1 wherein
$R^1$ is methyl;
$R^2$ is methyl;
$R^3$ is hydrogen;
L is a bond;
$R^6$ is $(C_5-C_{12})$heteroaryl, wherein the $(C_5-C_{12})$heteroaryl is pyridinyl, quinolinyl, or thienyl each optionally substituted with 1 substituent that is $(C_1-C_6)$alkyl or halogen; and
$R^7$ is absent.

8. The compound according to claim 1 that is
4-[3-(5-ethyl-2-thienyl)isoxazol-5-yl]-N-hydroxy-2-methyl-2-(methylsulfonyl)butanamide;
N-hydroxy-2-methyl-2-(methylsulfonyl)-4-(3-quinolin-2-ylisoxazol-5-yl)butanamide;
4-[3-(3-fluoropyridin-4-yl)isoxazol-5-yl]-N-hydroxy-2-methyl-2-(methylsulfonyl)butanamide;
N-hydroxy-2-methyl-2-(methylsulfonyl)-4-(3-quinolin-3-ylisoxazol-5-yl)butanamide;
4-[3-(3-fluoropyridin-2-yl)isoxazol-5-yl]-N-hydroxy-2-methyl-2-(methylsulfonyl)butanamide;
N-hydroxy-2-methyl-2-(methylsulfonyl)-4-(3-quinolin-4-ylisoxazol-5-yl)butanamide;
or a pharmaceutically acceptable salt thereof.

9. The compound according to claim 1 wherein
$R^1$ is methyl;
$R^2$ is methyl;
$R^3$ is hydrogen;
L is a bond, —$(CH_2)_n$—, —$(CH_2)_nO(CH_2)_p$—, —$(CH_2)_nS(CH_2)_p$—, —$(CH_2)_nNR^4(CH_2)_p$—, —$(CH_2)_nSO_2NR^4(CH_2)_p$—, —$(CH_2)_nCONR^4(CH_2)_p$—, or —$(CH_2)_nNR^4CO(CH_2)_p$—;
$R^4$ and $R^5$ are independently hydrogen, $(C_1-C_6)$alkyl, or $(C_3-C_8)$cycloalkyl;
n is 0, 1, or 2;
p is 0, 1, or 2;

$R^6$ is $(C_1-C_6)$alkoxy$(C_1-C_6)$alkyl, $(C_1-C_6)$alkoxycarbonyl, $(C_1-C_6)$alkylthiocarbonyl, $(C_3-C_8)$cycloalkyl, hydroxy$(C_1-C_{10})$alkyl, or $(NR^4R^5)$carbonyl, wherein the $(C_3-C_8)$cycloalkyl is cyclohexyl optionally substituted with 1 substituent that is hydroxy; and $R^7$ is absent.

10. The compound according to claim 1 wherein $R^1$ is methyl;
$R^2$ is methyl;
$R^3$ is hydrogen;
L is a bond, —(CH$_2$)—, —O(CH$_2$)—, —NR$^4$(CH$_2$)—, or —NR$^4$CO—;
$R^4$ and $R^5$ are independently hydrogen, $(C_1-C_6)$alkyl, or $(C_3-C_8)$cycloalkyl;
$R^6$ is $(C_1-C_6)$alkoxy$(C_1-C_6)$alkyl, $(C_1-C_6)$alkoxycarbonyl, $(C_1-C_6)$alkylthiocarbonyl, $(C_3-C_8)$cycloalkyl, hydroxy$(C_1-C_{10})$alkyl, or $(NR^4R^5)$carbonyl, wherein the $(C_3-C_8)$cycloalkyl is cyclohexyl optionally substituted with 1 substituent that is hydroxy; and
$R^7$ is absent.

11. The compound according to claim 1 that is

S-butyl({3-[4-(hydroxyamino)-3-methyl-3-(methylsulfonyl)-4-oxobutyl]isoxazol-5-yl}methyl)methylthiocarbamate;

N-hydroxy-4-[5-(9-hydroxynonyl)isoxazol-3-yl]-2-methyl-2-(methylsulfonyl)butanamide;

N-hydroxy-4-{5-[(1-hydroxycyclohexyl)methyl]isoxazol-3-yl}-2-methyl-2-(methylsulfonyl)butanamide;

ethyl({3-[4-(hydroxyamino)-3-methyl-3-(methylsulfonyl)-4-oxobutyl]isoxazol-5-yl}methyl)isopropylcarbamate;

{3-[4-(hydroxyamino)-3-methyl-3-(methylsulfonyl)-4-oxobutyl]isoxazol-5-yl}methyl butylcarbamate;

4-[3-(1-ethoxy-1-methylethyl)isoxazol-5-yl]-N-hydroxy-2-methyl-2-(methylsulfonyl)butanamide;

N-cyclohexyl-5-[4-(hydroxyamino)-3-methyl-3-(methylsulfonyl)-4-oxobutyl]isoxazole-3-carboxamide;

or a pharmaceutically acceptable salt thereof.

12. A pharmaceutical composition comprising a compound or pharmaceutically acceptable salt thereof according to claim 1 in admixture with at least one pharmaceutically acceptable excipient.

13. A method of treating a bacterial infection in a patient, the method comprising administering a therapeutically effect amount of a compound or pharmaceutically acceptable salt thereof according to claim 1 to a patient in need thereof.

* * * * *